United States Patent
Heid et al.

(10) Patent No.: US 8,299,789 B2
(45) Date of Patent: Oct. 30, 2012

(54) METHOD AND DEVICE FOR AUTOMATED GENERATION OF A FORMAL DESCRIPTION OF A MAGNETIC RESONANCE SYSTEM MEASUREMENT SEQUENCE, USING A SEQUENCE MODEL

(75) Inventors: Oliver Heid, Genzenhausen (DE); Thomas Kluge, Hirschaid (DE)

(73) Assignee: Siemens Aktiengesellschaft, Munich (DE)

( * ) Notice: Subject to any disclaimer, the term of this patent is extended or adjusted under 35 U.S.C. 154(b) by 566 days.

(21) Appl. No.: 12/549,460

(22) Filed: Aug. 28, 2009

(65) Prior Publication Data

US 2010/0090694 A1    Apr. 15, 2010

(30) Foreign Application Priority Data

Aug. 28, 2008 (DE) .................... 10 2008 044 828

(51) Int. Cl.
*G01V 3/00* (2006.01)
(52) U.S. Cl. ......................... 324/309; 324/314
(58) Field of Classification Search .................. 324/309, 324/307, 314, 318, 322
See application file for complete search history.

(56) References Cited

U.S. PATENT DOCUMENTS

| | | | |
|---|---|---|---|
| 4,707,661 A | | 11/1987 | Hoenninger et al. |
| 5,144,242 A | | 9/1992 | Zeilenga et al. |
| 5,519,320 A | * | 5/1996 | Kanayama et al. ........... 324/309 |
| 6,166,544 A | * | 12/2000 | Debbins et al. .............. 324/309 |
| 6,249,120 B1 | | 6/2001 | McKinnon et al. |
| 6,275,721 B1 | * | 8/2001 | Darrow et al. ................ 600/410 |
| 6,522,141 B2 | * | 2/2003 | Debbins et al. .............. 324/307 |
| 7,081,750 B1 | * | 7/2006 | Zhang ........................... 324/309 |
| 7,443,166 B2 | * | 10/2008 | Heid ............................. 324/322 |
| 8,115,484 B2 | * | 2/2012 | Heid et al. .................... 324/309 |
| 2008/0284431 A1 | | 11/2008 | Fishkin |

FOREIGN PATENT DOCUMENTS

WO   WO 2007/121020   10/2007

* cited by examiner

*Primary Examiner* — Louis Arana
(74) *Attorney, Agent, or Firm* — Schiff Hardin LLP

(57) ABSTRACT

A magnetic resonance sequence model that is a formal description of a measurement sequence is used to automate measurement sequence programming. The sequence model allows a system-independent specification of the measurement sequence for execution in a magnetic resonance scanner. The sequence model is as formal as possible; it is limited to the minimum required information for description of a measurement sequence without limiting the flexibility in the sequence programming. A method for formal description of the measurement sequence describes the measurement sequence by a number of parameters to be parameterized. The parameterization of the measurement sequence can ensue automatically from the formalized description of the measurement sequence, except for a set of parameters that are still be determined. For automatic generation of an executable measurement sequence, the method determines the parameters to be determined using a solver, under consideration of boundary conditions, so that a consistent set of parameters is created that completely describes the measurement sequence. This complete description of parameter values of the measurement sequence is then be translated automatically into a programming language that can be directly executed in the magnetic resonance scanner.

24 Claims, 15 Drawing Sheets

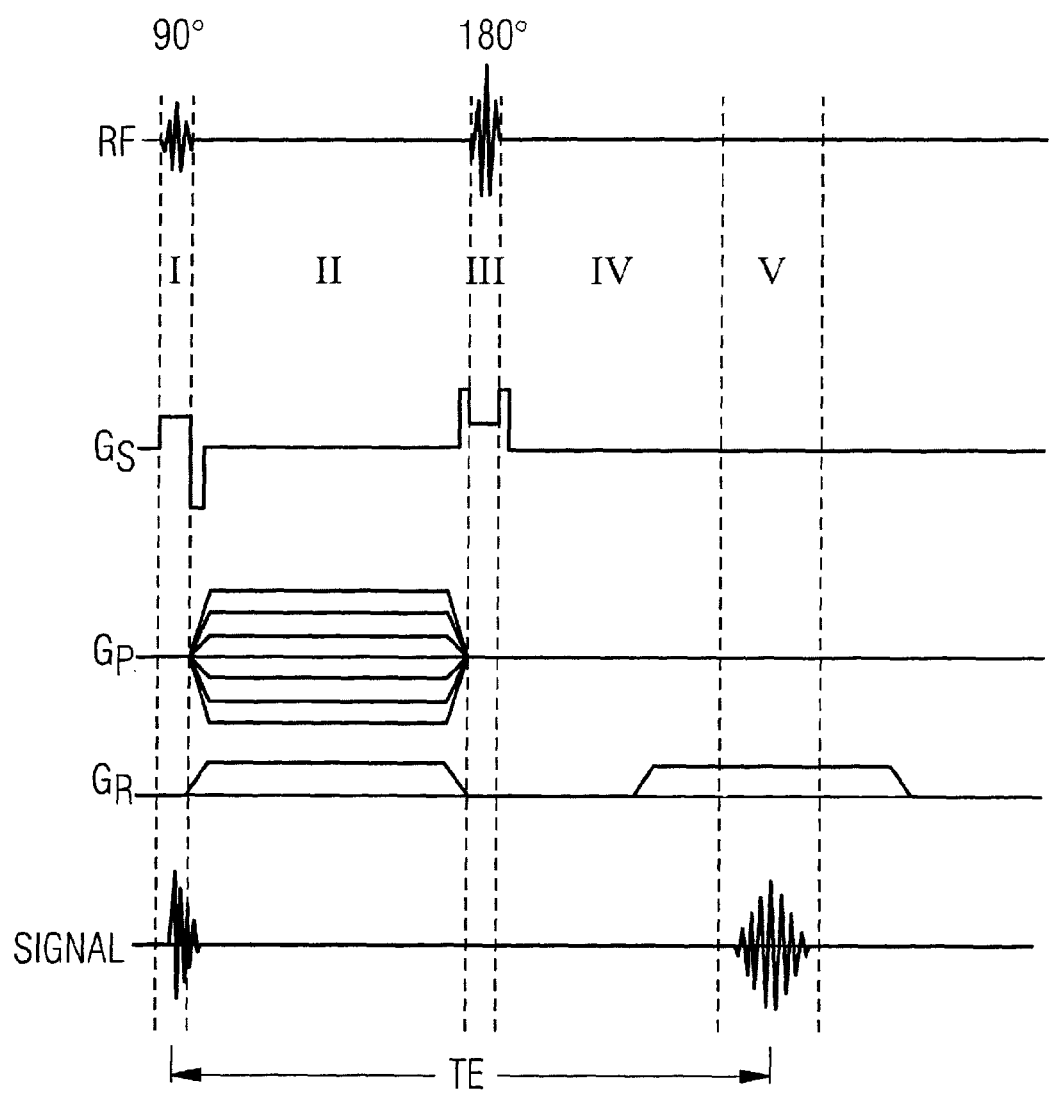

FIG 3A
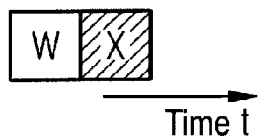
FIG 3B
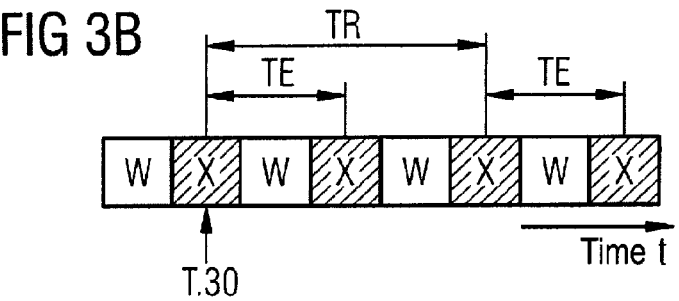
FIG 3C
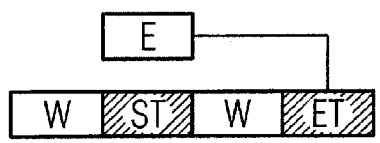
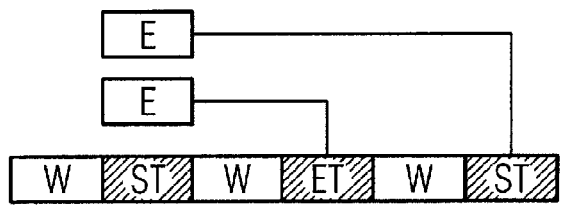
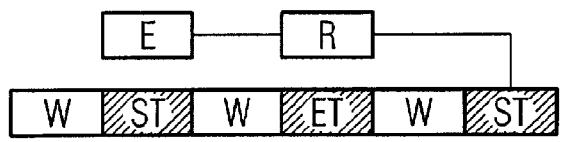
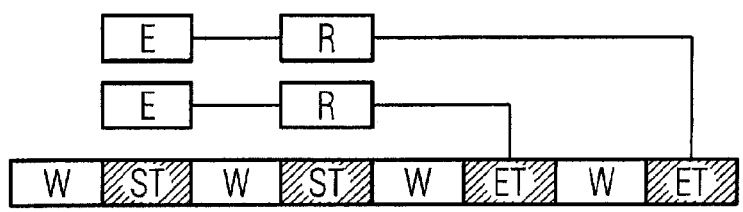
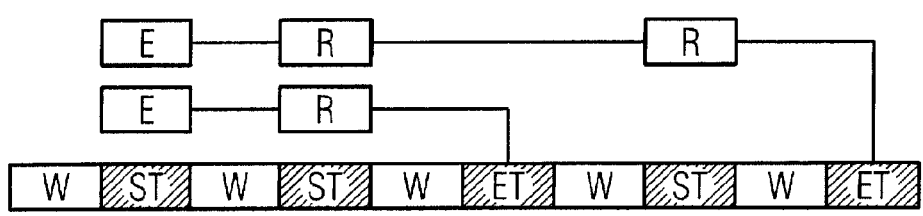

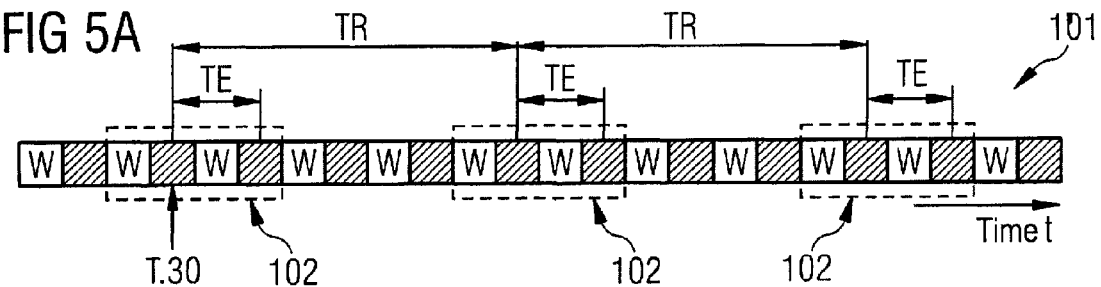
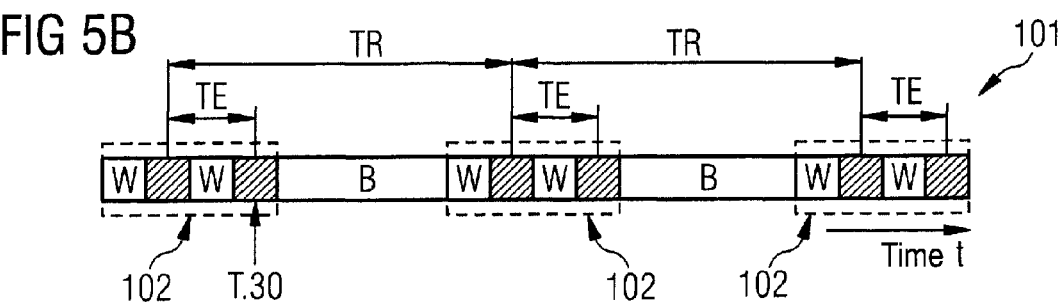
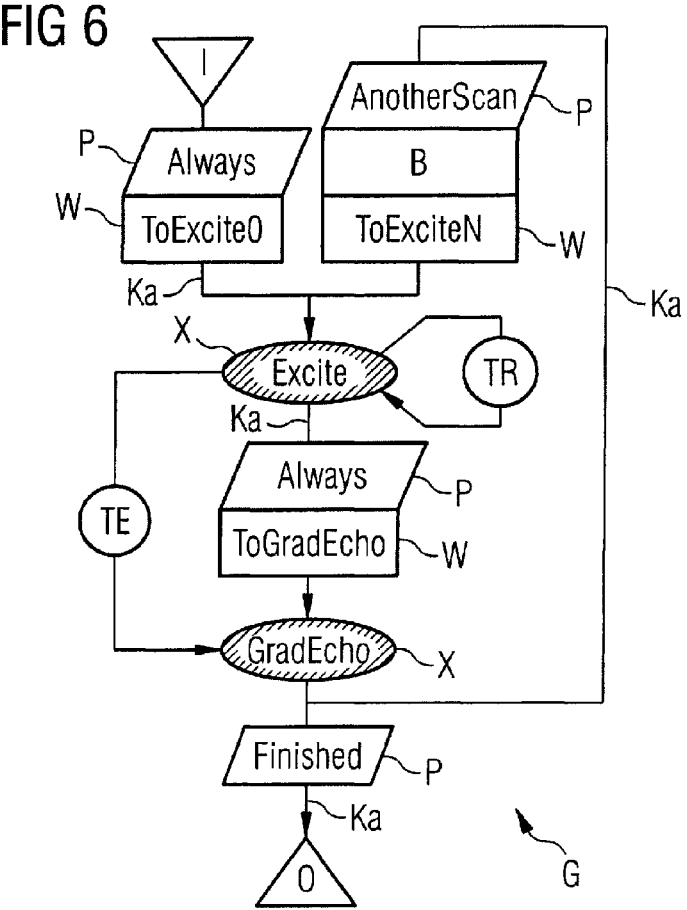

FIG 7A
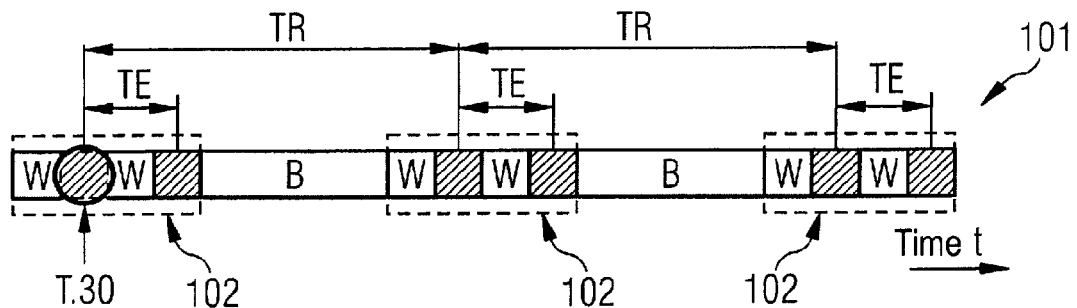
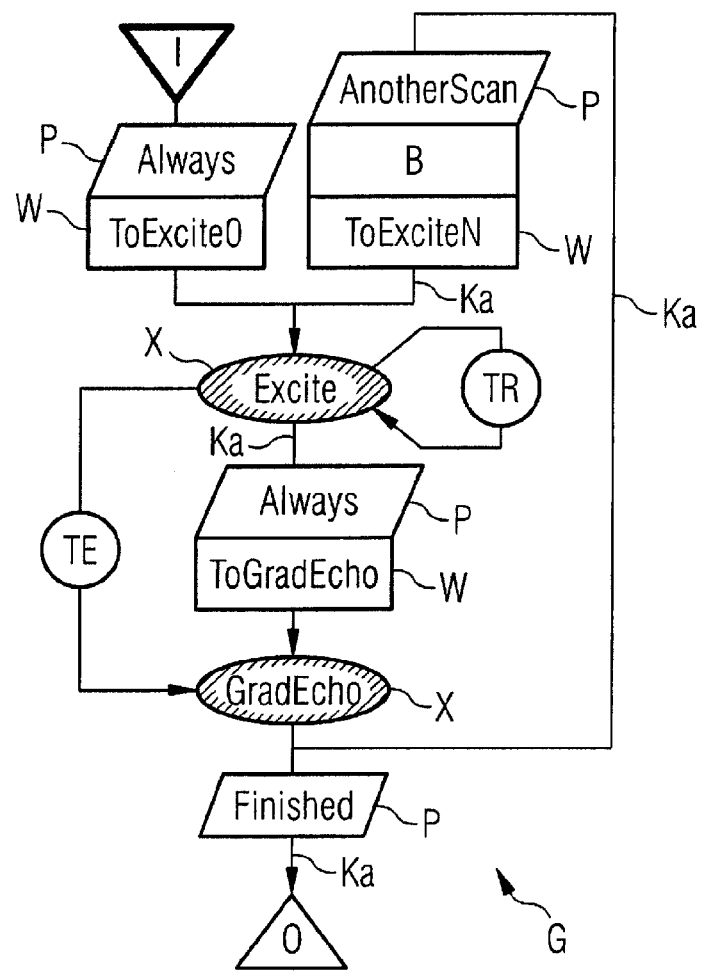

FIG 7B
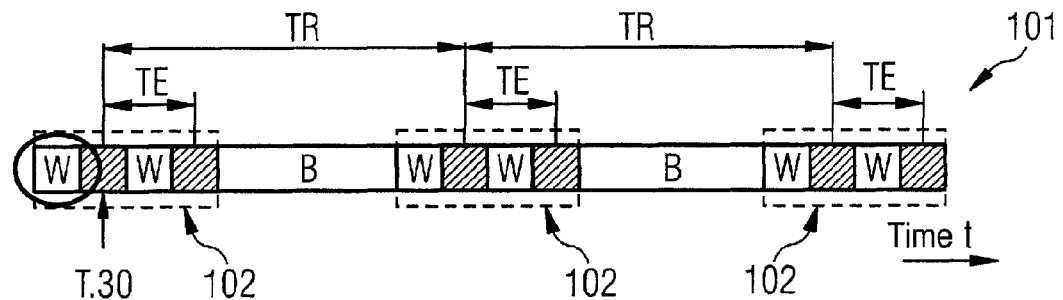
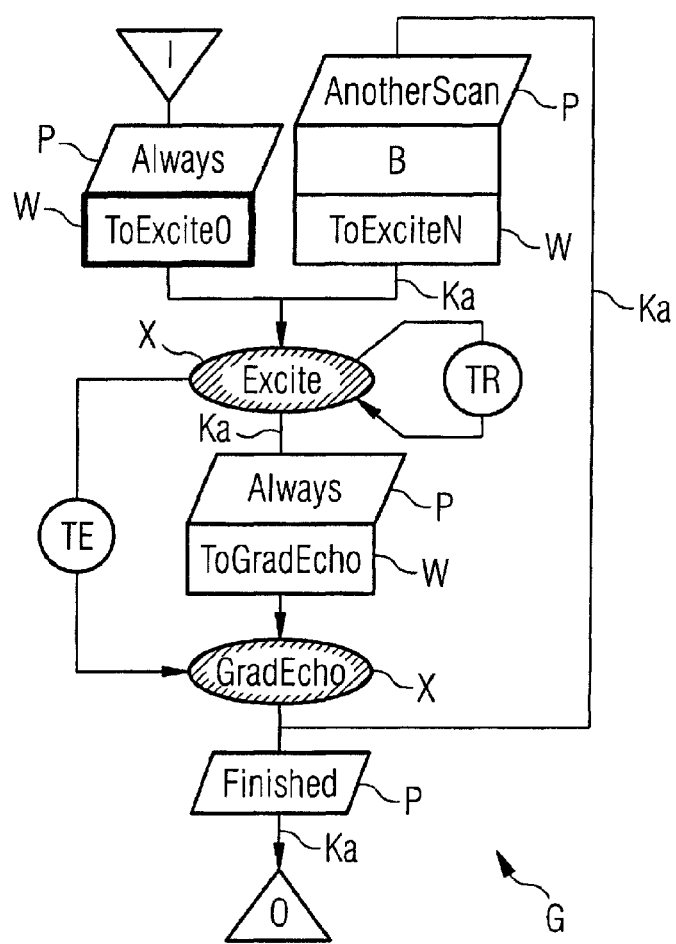

FIG 7C
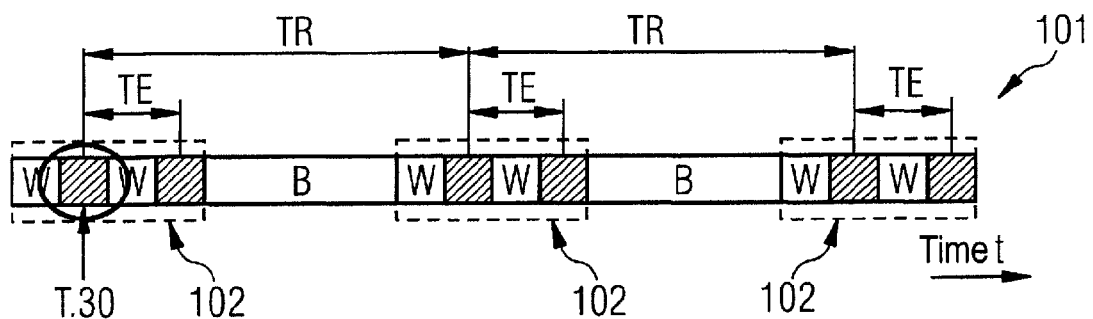
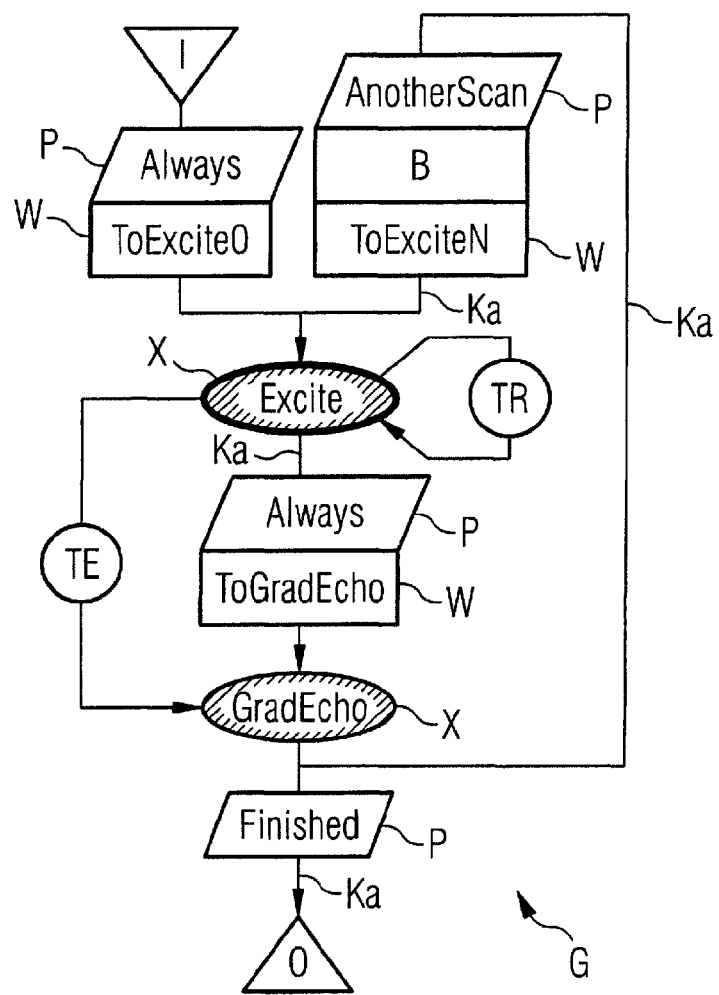

FIG 7D
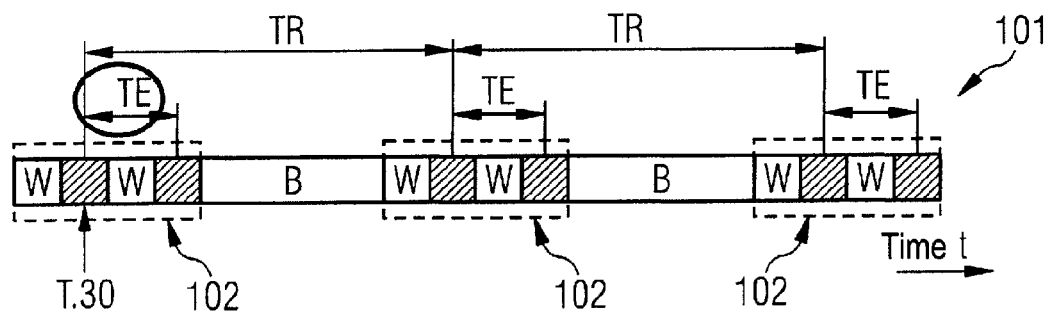
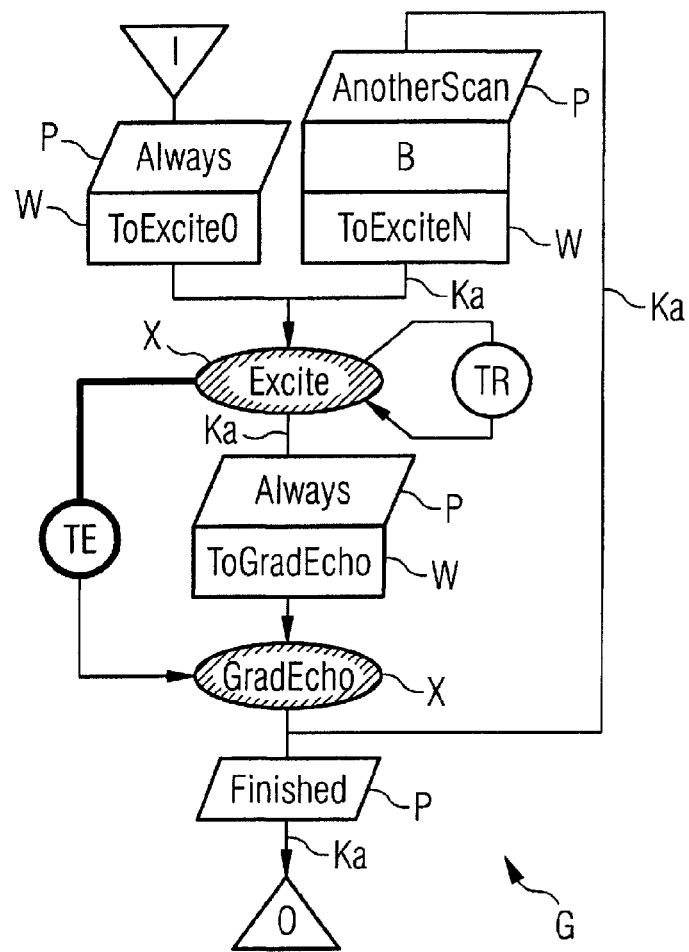

FIG 7E
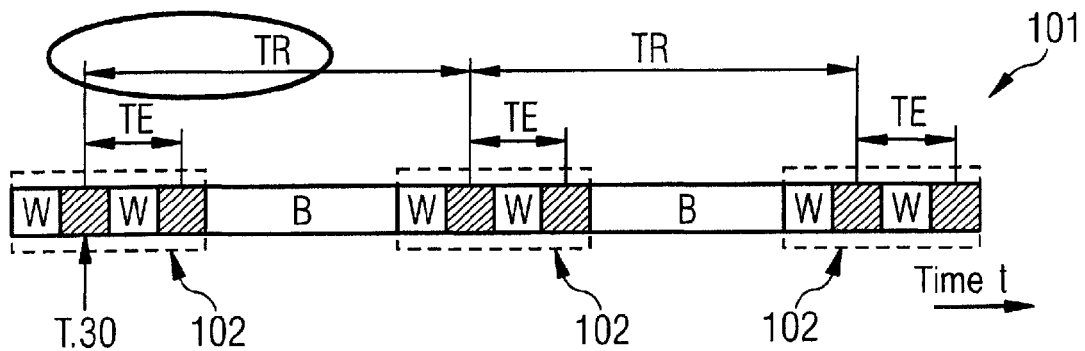
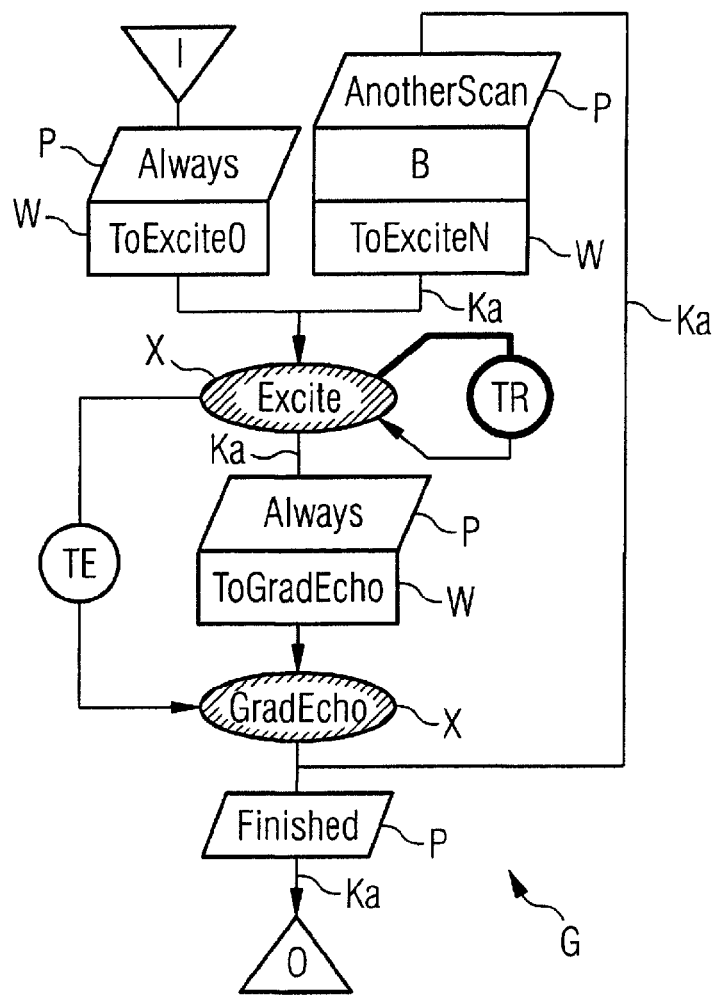

FIG 7F
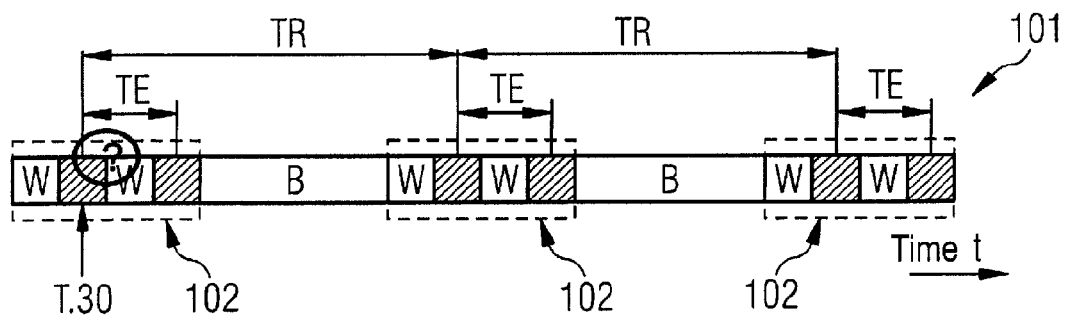
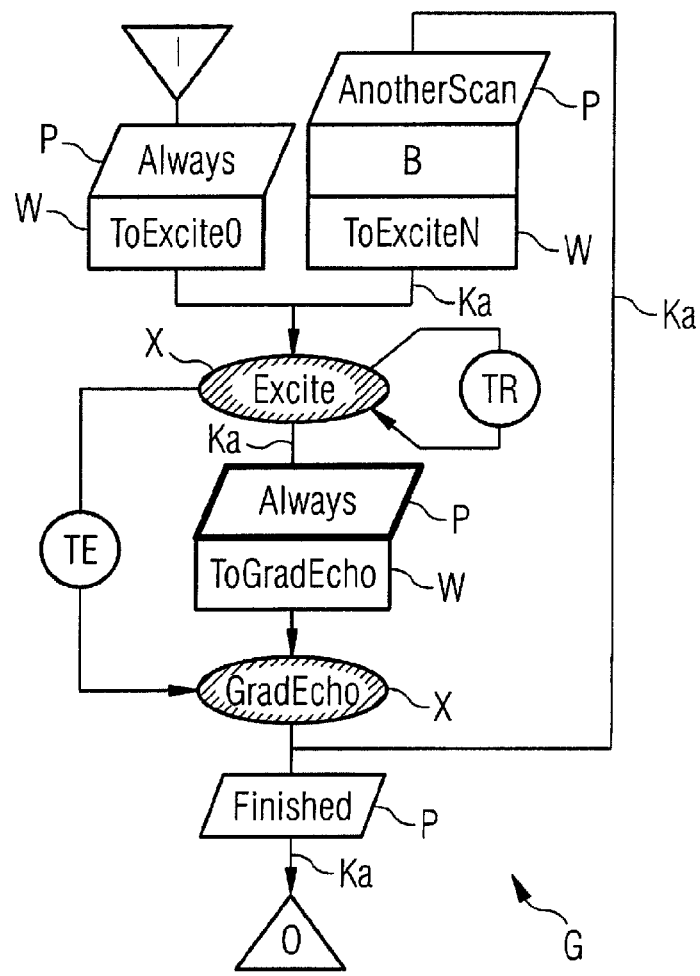

FIG 7G
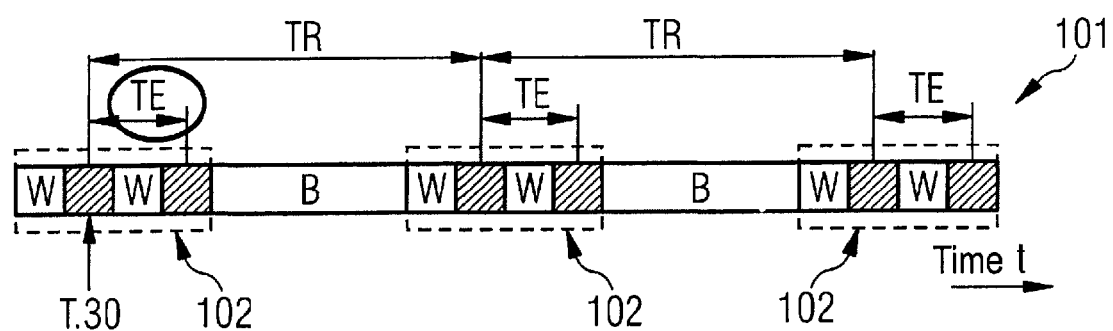
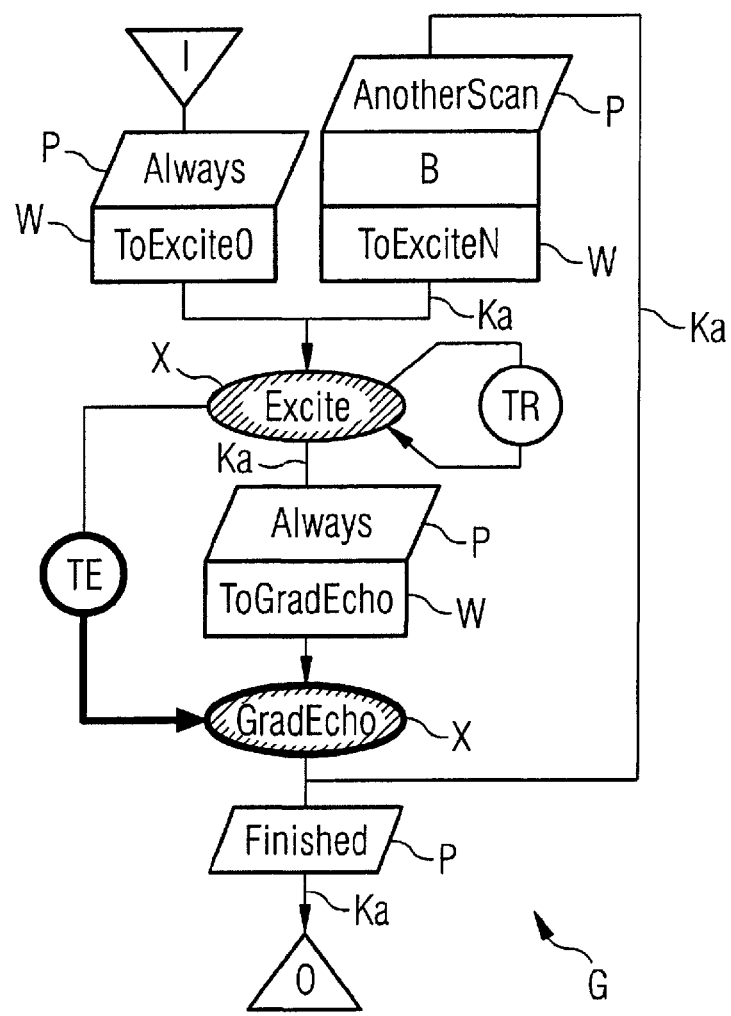

FIG 7H
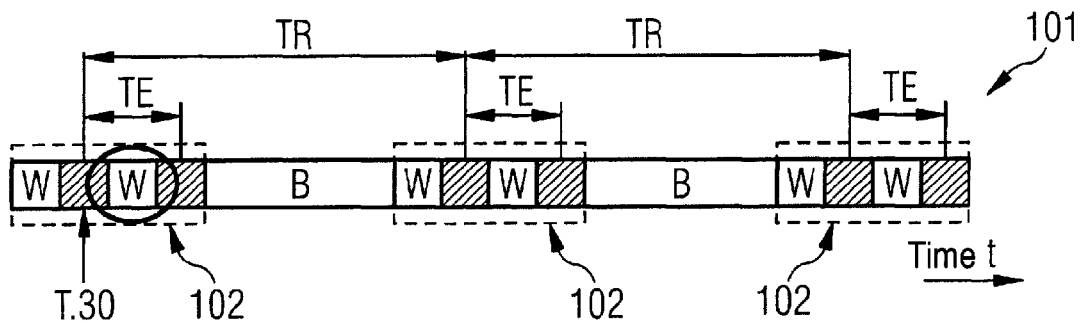
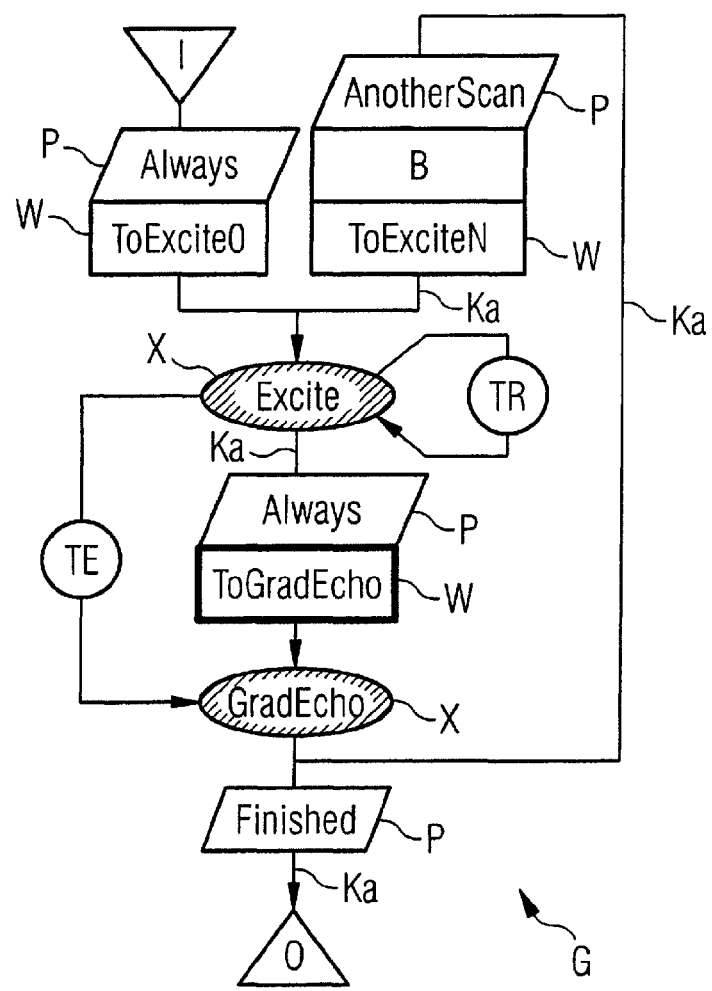

FIG 7I
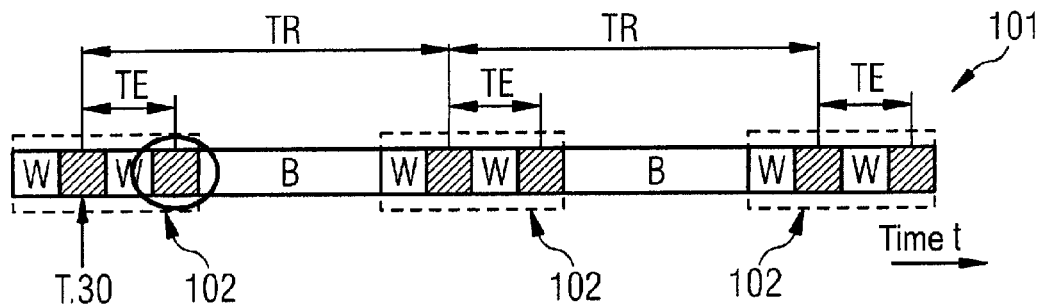
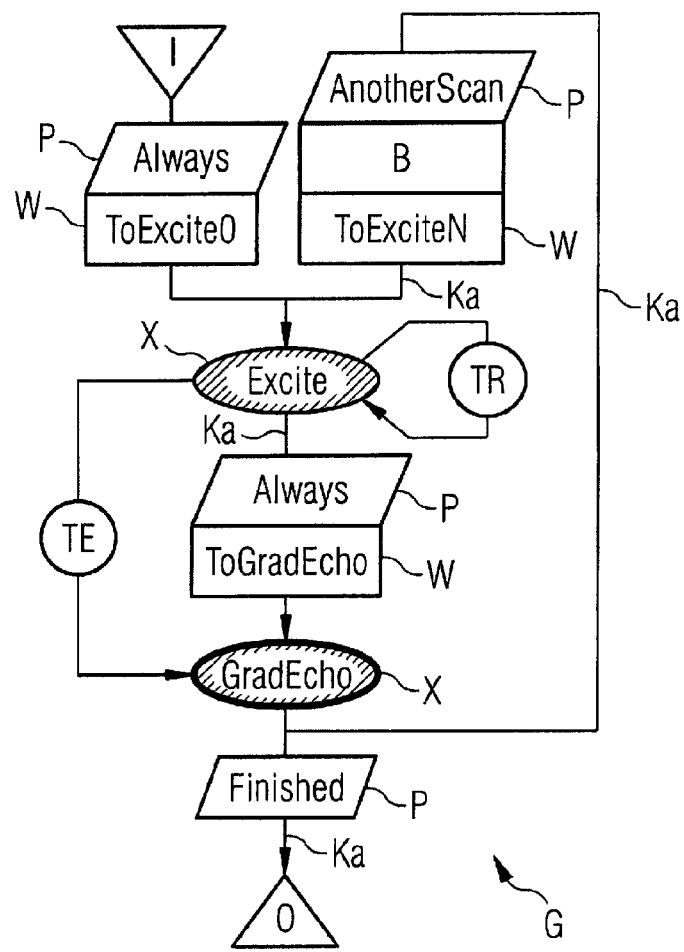

METHOD AND DEVICE FOR AUTOMATED GENERATION OF A FORMAL DESCRIPTION OF A MAGNETIC RESONANCE SYSTEM MEASUREMENT SEQUENCE, USING A SEQUENCE MODEL

BACKGROUND OF THE INVENTION

1. Related Application

The present application is related to an application filed simultaneously herewith, owned by the same Assignee, entitled "Method and Device to Generate a Measurement Sequence For Operating a Magnetic Resonance System That is Adapted to the Time Raster of the System," having U.S. Ser. No. 12/540,475.

2. Field of the Invention

The present invention is in the field of programming of measurement sequences for magnetic resonance. In particular, the invention proposes a formal description of a measurement sequence using a magnetic resonance sequence model, whereby the programming of measurement sequences for magnetic resonance can be largely automated.

3. Description of the Prior Art

Magnetic resonance (MR) scanners (also called nuclear magnetic resonance tomographs) today are a basic component of the clinical routine for examination of patients in hospitals. Moreover, magnetic resonance scanners can also be used for the examination of animals and/or biological samples.

Measurement sequences are necessary to control the MR scanner.

The generation of MR images in an MR scanner requires an exact, temporal workflow between the radio-frequency excitation of the spins, the spatial coding and the detection of the resonant response of the spin. The temporal workflow of the excitation, preparation and detection is called a pulse sequence or measurement sequence. A single segment of the measurement sequence can be classified according to its purpose. This division is designated as a time slice. A time slice is thus an established time segment within the measurement sequence that serves a specific purpose, for example the excitation of the nuclear spins. Time slices contain control instructions for the MR scanner. The time slices precisely establish what the MR scanner has to do and at which point in time. A series of time slices can be executed in the MR scanner because it contains all instructions and their temporal correlation to the control of the MR scanner. Alternatively, the execution of the time slices with a control unit connected with the MR scanner is also possible.

A measurement sequence can be executed as a series of time slices in the MR scanner. Within the measurement sequence for execution in an MR scanner, the time slices are joined seamlessly (i.e. without gaps). Each of the time slices has a specific length, and at least one pulse with a pulse shape is associated with every time slice. Each of the time slices can be associated with a type from the set: transmission type for transmission of RF power; reception type to detect the resonant response of the nuclear spins; and warp type to prepare the nuclear spins. Time slices of the transmission type are used as excitation pulses to excite the nuclear spins, to refocus the nuclear spins, and in a hybrid form that serves both for excitation and for refocusing. In addition to these, there are time slices in which RF energy is emitted and/or an RF signal is received. Moreover, RF pulses are known for the inversion of the nuclear magnetization, called inversion pulses.

Over the years many MR sequences or measurement sequences have been developed for different purposes. For example, it is possible to significantly affect the contrast of an image by the selection of a measurement sequence. The preparation of the spin system—for example by means of pulses for RF excitation, gradient pulses, wait times and so forth—has a decisive influence on the quality and property of the acquired MR image.

A measurement sequence for execution in an MR scanner in a clinical everyday situation typically is composed of 106 different time slices that are involved in a sensitive temporal correlation among one another. The creation of the measurement sequences has developed into its own field of MR physics.

Conventionally, measurement sequences for execution in an MR scanner have been prepared by a sequence programmer. This occurs in one of the known programming languages, normally C++, which describes all properties and the temporal sequence of the time slices. This means that the measurement sequence has conventionally been generated manually in order to exist in a completely parameterized form and with permissible parameter values for execution in the MR scanner.

The administration (management) of so many parameters is laborious and prone to error. Errors of the programmer in the sequence programming can lead, for example, to the situation that an MR examination of a patient is terminated by the MR scanner and/or a supervision module because, for example, necessary parameters are not populated with a value. Extensive (for example temporal) connections exist between individual parameters so that an MR image can be acquired. If these connections are not maintained, the desired MR image is not acquired. The checking of these extensive connections by the sequence programmer is very time-consuming and error-prone.

When a new measurement sequence for execution in an MR scanner is developed, the discovery of a permissible parameter set that generates the desired MR image is additionally a laborious process. The user of the MR scanner and/or the programmer must change individual parameters in many iteration steps until the parameter set contains permissible values that are matched to one another as a while so that the measurement sequence is executable in the MR scanner.

A need therefore exists to describe measurement sequences as concisely and comprehensively as possible. A measurement sequence description is thus sought. At the same time, such a concise description may not limit the freedom of the programmer to create new measurement sequences.

Moreover, a need exists for a method that automatically develops a measurement sequence in a form such that the measurement sequence is executable in the MR scanner. For current MR scanners, this can mean to automatically translate the measurement sequence specification into a series of time slices that can be executed in the MR scanner.

SUMMARY OF THE INVENTION

The present invention concerns a method for formal or formalized description of a measurement sequence. A sequence model is used for the creation of the formal description. The sequence model allows a very concise measurement sequence specification to be specified in the form of the formalized description. Moreover, this formal description of the measurement sequence is independent of the data acquisition system. This means that the formal description does not depend on the properties of the system in which the measurement sequence are to be executed. A greater degree of abstraction than before is therefore achieved in the description and programming of measurement sequences.

The invention moreover encompasses a method for the automatic translation of the measurement sequence into a series of time slices that can be executed in the MR scanner. The method determines from a formalized description a plurality of properties of the measurement sequence that effectively result automatically from the formal description. The programming effort for the measurement sequence programmer is therefore significantly reduced. The present invention thus significantly simplifies the control of MR scanners. The method according to the invention allows a measurement sequence that can be executed directly in an MR scanner to be generated starting from a formal MR sequence model.

A stream of control instructions to an MR scanner can be generated from the formal description using a solver, for example as a series of time slices. The series of time slices can then be executed directly in the MR scanner, whereby an MR examination is initiated. The use and function of a solver is explained in the following:

The object of the invention is in particular achieved by a method for the formal description of a measurement sequence to execute a magnetic resonance scanner, a method to automatically generate a measurement sequence for execution in an MR scanner, a computer-readable medium that implements a method for formal description of a measurement sequence and/or a method for automatic generation of a measurement sequence for execution in an magnetic resonance scanner when it is executed in a computer, and a system for automatic generation of a measurement sequence for execution in a magnetic resonance scanner.

The object is in particular achieved by a method for formal description of measurement sequences for execution in an MR scanner.

The method according to the invention is based on a sequence model in which the measurement sequence can be presented as a directed graph. The sequence model uses blocks for the construction of the directed graph. The directed graph comprises nodes, edges and properties of the edges for workflow control.

The sequence model allows the measurement sequence to be automatically parameterized from the directed graph except for a set of specific parameters.

"Parameterizable" means that the parameters which describe the measurement sequence are known at least as placeholders. A list of all parameters that are necessary for a complete description of the measurement sequence can thus be specified. In particular, this list results from the directed graph.

The set of parameters to be determined is characterized in that the parameter values for these parameters must be predetermined; normally by the user.

As used herein, a "formal description", means a depiction of the physical MR correlations in a formal form. Within the scope of this invention, a formal description is disclosed that encompasses all possible measurement sequences. The formal description thus generically allows the description of all possible measurement sequences for the execution in an MR scanner. This means that freedom in the measurement sequence programming is retained by the programmer of the measurement sequence; however, a measurement sequence is described within the framework of a formal description, i.e. in a type of programming language.

The measurement sequence can be parameterized (except for a set of parameters to be determined) from the formal description or the sequence specification language.

In the following, a block represents a time slice of a measurement sequence. However, the significant difference between the time slice and the block is that the properties of the block are not completely established. A block is therefore a placeholder or a container for a time slice without concrete duration, while the time slices have a concrete duration.

Therefore the block provides all properties that describe a time slice, at least as a placeholder for the concrete parameter value. In this sense a block represents an abstraction of the concrete time slice within a measurement sequence.

In order to obtain a time slice from a block, all properties (i.e. all parameters) that describe the block in terms of its properties must be defined. This means that these parameters must be populated with specific values.

Within the scope of the sequence model that is used, blocks of one of the elements from the group of warp block, X block and pause can be used. A warp block (also abbreviated as a W block) is representative of a time slice of the warp type. In contrast to this, an X block is representative of a time slice during which RF power is emitted and/or an RF signal is received. The modeling and identification of pauses is important for the interleaving of measurement sequences. They mark time windows in which the execution of at least portions of an additional measurement sequence can be executed but do not need to be executed.

In the disclosed sequence model, blocks join seamlessly and without overlap. Relative time correlations between individual blocks can also be formulated within the framework of the sequence model, for example in the form of sequence times, as is explained later.

An additional significant concept of the proposed sequence model is to combine warp block units and X block units into one unit, what is known as a WX block. The decision to consider WX blocks in the sequence model is only one possibility; however, it turns out to be very reasonable. This allows very concise and elegant measurement sequence specifications.

Naturally, sequence models in which other blocks are also comprised as WX blocks would also be conceivable. However, such a sequence model would not allow anywhere near as concise a representation of measurement sequences as is the case for the method according to the invention. Therefore, the sequence model described above that considers WX blocks as a unit is described.

Starting from the sequence model, a measurement sequence can be shown as a directed graph in an additional step.

The nodes of the directed graph are formed from the group consisting of X blocks, entrance point and exit point. The decision to select X blocks as nodes of the directed graph in addition to entrance point and exit point is arbitrary. It would likewise be possible to describe warp blocks as nodes of the directed graph. However, in this case a formal description of a measurement sequence would be more complicated since sequence times (for instance the echo time) do not result as comfortably as a time measurement between nodes of the directed graph.

The depiction of the formal description based on the sequence model as a directed graph is only an example. Any other formal description based on the sequence model, for instance in pseudo-code or in a programming language (for example C++) would likewise be possible. The selection of the formal description is therefore merely a syntactic choice. A translation from the one formal description into the other formal description can occur. In this sense the presentation of the measurement sequence as a directed graph is merely comfortable for a user and/or the sequence programmer since it can be composed very concisely.

Directed graphs can be used in order to depict workflows or algorithms. In informatics they are known to describe automata, for example. In light of this background, the presentation of a measurement sequence as a directed graph represents a further abstraction of a series of time slices that can be executed in an MR scanner. Via a run through the directed graph the measurement sequence represented as a directed graph can be depicted in its temporal sequence on a global time axis. The concrete temporal workflow of the measurement sequence represented as a directed graph is still not completely defined. Initially only relative temporal connections are established, for example the sequence times between specific X blocks and the seamless joining of the blocks with one another without overlapping. The progression of the directed graph normally supplies a meta-time plan for the workflow of the measurement sequence. The concrete translation of the meta-time plan of the measurement sequence into a series of time slices is achieved by solving the timing problem. According to the invention, a solver can be used for this purpose.

The entrance point in time identifies the entrance into the graph. The exit point in time marks the end of the workflow in the graph.

In a directed graph, nodes are connected via edges of the directed graph. These edges correspond to transitions as they are known to those skilled in the art in the field of automation theory.

A workflow or run through the directed graph from the entrance point to its exit point describes the measurement sequence. The run-through means the progression of the edges of the directed graph under consideration of path controls in the directed graph as well as the properties for workflow control of the directed graph. The selected form of the directed graph as a depiction of the measurement sequence has proven to be a very elegant form of presentation since it is no longer necessary to explicitly note all blocks of the measurement sequence.

In addition to the nodes and transitions or edges of the directed graph, properties of the edges for workflow control of the directed graph are necessary for the formal description or, respectively, modeling of a measurement sequence according to the invention in the form of a directed graph. These properties of the edges are used in order to represent additional properties and connections in a measurement sequence in their depiction as a directed graph.

The properties of the edges for workflow control of the directed graphs can be: a warp block, a time measurement, a pause and/or a path control. A warp block serves for preparation of the nuclear magnetic resonance system. A pause or a pause block is a time segment during a measurement sequence in which no action is executed; essentially, the MR scanner thus waits. A "path control" is a query that must be satisfied so that a specific segment of the directed graph can be executed.

The method according to the invention furthermore comprises edges between the nodes that are provided by the group consisting of:
   a transition from the entrance point via a path control to a warp block, and from there to an X block,
   a transition from an X block via a path control to an exit point,
   a transition from an X block via a path control to a warp block, and from there to an X block,
   a transition from an X block via a path control and a pause to a warp block, and from there to an X block, and
   a transition from an X block via a time measurement to an X block.

The edges therefore describe possible transitions, i.e. transfers between individual nodes of the directed graphs.

According to the present invention, X blocks of the transmission type can represent an excitation pulse, a refocusing pulse, an inversion pulse or a hybrid made up of excitation and refocusing pulses. An excitation pulse is an RF pulse that excites the spin system. A refocusing pulse reestablishes the coherence of the nuclear spins. Inversion pulses are used to invert the nuclear magnetization. Moreover, there are also X blocks of the transmission type that represent a hybrid of excitation and refocusing pulses. Transmission pulses of the hybrid form are in particular of interest in connection with stimulated echoes. Transmission pulses of the hybrid type serve to fold the non-transversal magnetization back into the transversal plane so that it can be detected as a signal. A more detailed explanation is available in Hennig, J., "Echoes—How to Generate, Recognize, Use or Avoid them in MR-Imaging Sequences" in Concepts in Magnetic Resonance 3 (1991), 125-143.

According to the present invention, only one of the path controls within the directed graph may ever be satisfied. Such a directed graph (and therefore a measurement sequence) can contain a plurality of path controls. With the requirement that only one of the path controls may ever be satisfied, it is ensured that only one (as well as which) edge of the directed graph may be executed at branching point. In other words, path controls determine the workflow of the directed graph.

Through the path controls it is ensured that only one of the edges of the directed graph is executed. The path controls thereby represent the functionality of a logical, exclusive OR-function, also called XOR.

The time measurements are always an element from the group consisting of a time duration of an individual X block, a sequence time and a sequence start time. The duration of an X block is provided by the start and the end of the respective X block. A sequence time is measured between the centers of two X blocks. Examples of such sequence times are the echo time, the repetition time or the inversion time. Sequence times represent global properties of a measurement sequence. Moreover, a sequence start time that describes the point in time at which the center of the first X block is reached within a measurement sequence is necessary to describe the measurement sequence within the framework of the sequence model. The point in time of all X blocks and all warp blocks within the directed graphs can be determined with these three types of time measurements. These three types of time measurements are sufficient to describe the relative temporal correlations of the blocks within the measurement sequence as they are used in MR imaging.

In an additional embodiment of the method according to the invention, indices regarding each of the X blocks are determined that are defined from the run through the directed graph. Strictly speaking, it is one index for each WX block.

Moreover, variables regarding each of the warp blocks and each of the X blocks are determined from the directed graph. A gradient moment of the zeroth order with regard to each center of every X block of the transmission type and/or reception type can also be determined from the directed graphs.

As used herein "indices", means a running index across all WX blocks via which it is possible to uniquely identify each of the X blocks and each of the warp blocks within the sequence. In other words, the index can be understood as a reference (or informally as a "house number") of the X block, and therefore also of the associated warp block.

As soon as the index regarding each X block is known, an association of variables with every X block and every warp block can be produced from the directed graph. This means that the physical situation within an X block and within a warp block can be described. Thus the gradient moment of the zeroth order at every center of each X block and/or of each warp block can be directly determined from the association of indices and variables.

Here it is also true that the run through the directed graph is sufficient in order to directly specify this information for each of the blocks in the directed graph.

In a further embodiment, the method additionally includes a step to determine sequence equations from the run through the directed graph. Sequence equations for the measurement sequence can likewise be determined via the indices and variables already predetermined for the X blocks and the warp blocks within a measurement sequence. This means that all sequence equations for the measurement sequence are provided in parameterized form via the specification of the directed graph.

According to a further embodiment of the method, the method can also include a step to determine a path for echo creation a each X block of the transmission type or reception type. A path for echo creation thereby consists of a series of excitation pulses and/or inversion pulses and/or refocusing pulses and/or hybrids. The paths for echo creation result from the run through the directed graph. With regard to the paths for echo creation, refer to the publication by Hennig that was already cited. The path for echo creation can be elegantly determined from the run through the directed graph. The path for echo creation can be represented by an echo specification, as is detailed later.

In an additional embodiment, a gradient moment of the first order can be determined at every center of every X block of the transmission type and/or reception type from the run through the directed graph. It is thus possible to imprint a flux compensation and/or a flux coding in the measurement sequence. Gradient moments of the first order are known to those skilled in the art and are in particular relevant for the speed-dependent portions of the signal via which it is possible to compensate for signal components that result due to flowing matter (for example flow of liquor fluid and/or blood) and/or to very specifically code (i.e. depict) those portions of the signal in acquired MR images. In this context, coding means the depiction of signal portions in an MR image.

In a further embodiment, the method according to the invention comprises a determination of gradient moments of a higher order relative to ever center of every X block of the transmission type and/or reception type. The determination of gradient moments of a higher order is likewise possible from the run through the directed graph. The depiction of the measurement sequence as a directed graph therefore again turns out to be a very useful tool for modeling physical properties of the measurement sequence, for example of gradient moments.

In a further embodiment, the method according to the invention allows diffusion weightings to be determined from the run through the directed graph for each of the X blocks of the transmission type and/or reception type. "Diffusion weightings" means a strong preferred direction of the signal or of the signal propagation, for example. Such preferred directions can be predetermined by the anatomy of the patient. The flow of matter and signal is much greater along the direction of an artery than any flow of signal transversal to the wall of the artery. Nevertheless, a diffusion weighting in images approximately transversal to the wall of the artery is of great interest for diagnostic purposes since it provides information about the status of the vasculature. Such findings are relevant for diabetes patients, for example. The diffusion weighting is also of interest for what are known as MR fiber tracking studies.

The invention furthermore provides a method for automatic generation of a measurement sequence for execution in a magnetic resonance scanner according to claim 15. The programming of a measurement sequence can therefore be even further automated. This method assumes a formal description of a measurement sequence according to any of the claims 1-14, whereby the measurement sequence is present in parameterized form except for a set of parameters to be determined and can be depicted as a directed graph.

Due to the formal description, a set of parameters is left to be determined. More precisely, a set of parameters for which a plurality of solutions would be possible remains to be determined. Initially only the relative temporal relationships of the blocks relative to one another (and therefore of the time slices represented by the blocks) are also provided from the blocks in the directed graphs. Specific timing values for each of the blocks are also missing.

It is an object of the method for automatic generation to populate precisely this set of undefined parameters with concrete, wholly defined parameter values. In the method according to the invention for automatic generation of a measurement sequence, this is achieved under the consideration of boundary conditions that are to be satisfied to execute the measurement sequence. According to the invention, the timing values are determined by a solver. A solver is typically a software module that finds numerical solutions for a mathematical problem. For a solver as it can be used to solve the timing problem in MR imaging, for instance; refer to the German Patent Applications DE 102 13 848 A1 and DE 10 2006 034 397 B3 by the applicant. When the solver finds the solution, a plurality of parameters are still open. This plurality comprises temporal arrangement, timing, type and number of measurement sequences or, respectively, sub-sequences, as explained in the following. Every single parameter of the sub-sequences or, respectively, of the measurement sequences can be determined by the solver. This is discussed for the determination of timing values by way of example within the scope of this disclosure.

The method also includes an automatic translation of the formal description of the measurement sequence into a series of time slices that can be executed in a magnetic resonance scanner. This means that each of the blocks within the measurement sequence is to be provided by the solver with concrete values. Therefore all parameters of all blocks within the measurement sequence are provided with concrete values. Each of the blocks is therefore parameterized and represents all information that describes a time slice.

Automatic translation of the formal description of the measurement sequence is to be understood such that the formal description can be translated by a computer or by following a translation program, even without interaction by the user. The translation can be conducted by a translation module. This means that all properties of the measurement sequence are known. In other words, the solver determines those timing values that—first—are permitted and that—second—satisfy the boundary conditions. The set of parameters to be determined is filled with values that both satisfy the boundary conditions and are an acceptable solution to the timing problem. Such solutions are typically a problem with many variables. It is the task of the solver to find an acceptable solution. Insofar as there is no permissible solution that satisfies all relative time correlations of the blocks and the boundary conditions at the same time, an interaction with the user becomes necessary. An interaction with the user only occurs in the event that the solver cannot find any such solution. However, the number of necessary user interactions to generate a measurement sequence is significantly reduced by the method according to the invention. Using the method according to the invention for automatic translation, a manual input is necessary only when no permissible solution can be found with the predetermined values and limitations. An additional, significant advantage of the automatic translation of the formal description of the measurement sequence is, for example, that the tendency toward error in the code in the programming language which makes the measurement sequence executable in a magnetic resonance scanner is clearly reduced.

The method according to the invention can furthermore include steps for interleaved execution of measurement sequences. A measurement sequence includes many different individual MR measurements, for example the simultaneous acquisition of data from multiple slices. The acquisition of a single slice could be formulated as a single module, for example. Multiple instances of the individual module are then necessary for acquisition of multiple slices and must be interleaved for simultaneous execution of the instances so that they can be executed without overlap. Such a module within the measurement sequence is designated as a sub-sequence. A sub-sequence is a reasonable subset of WX blocks within a measurement sequence. A measurement sequence therefore is composed of at least one sub-sequence.

The possibility to consider sub-sequences within a measurement sequence in isolation is reasonable. The considered measurement sequence can thus be sub-divided into a plurality of smaller problems that are easier to solve. If a measurement sequence is spoken of in the following, a single sub-sequence can therefore also be intended. Measurement sequence can likewise designate the complete examination of a patient.

The directed graphs within this disclosure show only directed graphs that represent sub-sequences. Naturally, for a complete MR examination of a patient it is also possible to specify a directed graph that is normally composed of a number of directed graphs that represent the sub-sequences.

Sub-sequences contain indivisible superblocks. The smallest indivisible superblock within a measurement sequence is a WX block. The WX block may not be interrupted since otherwise the coherence of the nuclear spins is distorted and a defined RF signal is no longer generated. In addition to the WX block, there are larger indivisible superblocks that likewise may not be interrupted or divided. Indivisible superblocks within a sub-sequence are characterized in that they are connected by a pause in the corresponding directed graph, wherein the sub-sequence comprises a single superblock in the event that a sub-sequence does not comprise any pauses.

The method according to the invention for interleaved execution of measurement sequences initially includes the provision of multiple measurement sequences. At least one sub-sequence is subsequently identified within a first measurement sequence of the multiple measurement sequences. The identified sub-sequence comprises pauses. Sub-sequences are then determined from the respective other measurement sequences. "Respective other measurement sequence" means any of the provided measurement sequences except for the first measurement sequence. For interleaved execution of the measurement sequences, at least one of the determined sub-sequences is executed without overlap during the pauses of the respective first measurement sequence. In other words, it must thus be ensured that the sub-sequence inserted into the pauses of the first measurement sequence are always situated with their indivisible superblocks in the pauses of the first measurement sequence. Pauses between the indivisible superblocks are the time window during which the execution of additional sub-sequences is possible at all.

According to a further embodiment of the method according to the invention, boundary conditions are predetermined, wherein boundary conditions include at least one element from the group:

Contrast specifications. These are those specifications that determine the contrast of the acquired magnetic resonance image, for example $T_1$ contrast, $T_2$ contrast and fat suppression.

Image resolution specifications. These are those specifications that result from the desired resolution for a slice. For example, if multiple slices are acquired in the head near the cranium, the relevant surface per slice is always smaller with increasing proximity to the cranium until it ultimately contracts to a point. It is thus by all means reasonable to take such image resolution specifications as they result from the anatomy (for example) into account. Therefore the necessary storage requirement and the gradient strength that is required in order to generate a corresponding resolution can be adapted. Additional specifications are position specifications for at least one slice that should be acquired in an image. Thus where in the body this image is acquired (which is normally apparent solely from the diagnostic question) also places a role.

Hardware limitations arise from permissible load cycles for the gradient amplifier, for example, as well as for the edge steepness of the gradients, since specific limit values may not be exceeded or, respectively, a too-steep edge would lead to the overload of the power amplifier.

Minimization of the measurement time is an additional typical boundary condition that is desired in order to acquire images of the patient in as little time as possible. This in particular applies for examinations of the beating heart or what are known as breath-hold acquisitions, thus those acquisitions in which the patient holds his breath. Therefore very clear maximum values for the duration are predetermined for image acquisition that a measurement sequence must execute for this purpose. Entirely apart from this, there are naturally also economic motivations for a minimization of the measurement time, as already stated above.

Patent safety regulations. For example, these result from the risk of peripheral nerve stimulation that can be a result of too-steep gradients. Such a peripheral nerve stimulation is uncomfortable for the patient because it leads to involuntary movements of the members of the patient. An unwanted movement of the patient can also significantly degrade the acquisition of an MR image since the acquired image is then blurry. Moreover, the RF power absorbed by the patient may not exceed specific limit values since otherwise burns are inflicted on the patient. Such limit values for the tissue-specific absorption rate are predetermined and lie in the range of 4 watts per kilogram of body weight, for example.

Some of the boundary conditions that are to be satisfied can be those that are already predetermined by the hardware or are monitored by the hardware itself by means of what are known as monitoring modules (watchdogs). In the actual progression of the measurement sequence, these monitoring modules would ensure that limit values are not exceeded. If such a monitoring condition were violated in the progression of a measurement sequence, the entire measurement sequence is terminated. It is first of all uncomfortable for the patient, and moreover valuable scanner time is lost because a measurement must be restarted, hardware must be exchanged under the circumstances etc. By the monitoring of and compliance with such boundary conditions, in the automatic translation of the measurement sequence into time slices it is ensured that such unwanted interruptions of a running measurement sequence by the monitoring modules is avoided as much as possible.

The step of the automatic translation of the formal description into a programming language can take place in a further embodiment of the invention. This step of the automatic translation significantly reduces the tendency towards error of the programming of a measurement sequence in a programming language. For modern measurement sequences approximately $10^6$ parameters are necessary that must be populated with values (in particular permissible values). A programmer tends to be strenuously required to set all these values correctly.

The invention also encompasses a device for formal description of a measurement sequence for execution in a magnetic resonance scanner.

The invention also encompasses a device for automatic generation of a measurement sequence for execution in an MR scanner.

The above embodiments, and all advantages thereof, which have been described in connection with the method according to the invention are also applicable to the device, the computer-readable medium encoded with programming instructions and the magnetic resonance system in accordance with the present invention.

The invention also encompasses a system for automatic generation of a measurement sequence for execution in an MR scanner. The system includes a magnetic resonance scanner, a user interface and a device for formal description of a measurement sequence for execution in a magnetic resonance scanner.

The system can also optionally include a device for generation of a measurement sequence for execution in a magnetic resonance scanner.

Measurement sequences can be executed in the MR scanner. The user interface is designed for interaction with the user of the MR scanner. The user interface can in particular be required to start a measurement sequence, to interrupt a measurement sequence or to query the user in the event that no permissible values for the timing problem can be found under the predetermined boundary conditions.

Therefore the two devices can already be realized in this system. One or both of the devices can thereby alternatively already be fashioned as an integral component of the MR scanner and/or as software modules.

The system can include a device for formal description of a measurement sequence that should be executed in a magnetic resonance scanner. It is by all means possible to already execute the entire processing chain of the method, from the formal description through the automatic generation, in the magnetic resonance scanner and/or in the system according to the invention, and/or in a control unit connected with the magnetic resonance scanner.

BRIEF DESCRIPTION OF THE DRAWINGS

FIG. 2 shows a spin echo sequence as a series of time slices.

FIG. 3A shows a WX block as an elementary unit of the sequence model according to the invention.

FIG. 3B shows a sequence description as a series of WX blocks.

FIG. 3C shows the series of W blocks and X blocks for some known measurement sequences.

FIG. 5A shows a sub-sequence embedded into a stream of WX blocks.

FIG. 5B identifies the sub-sequence and pauses from the series of WX blocks shown in FIG. 5A.

FIG. 6 shows a directed graph that represents a gradient echo measurement sequence.

FIGS. 7A through 7I show the individual steps to acquire a gradient echo from the corresponding directed graphs.

DESCRIPTION OF THE PREFERRED EMBODIMENTS

Figure 1:
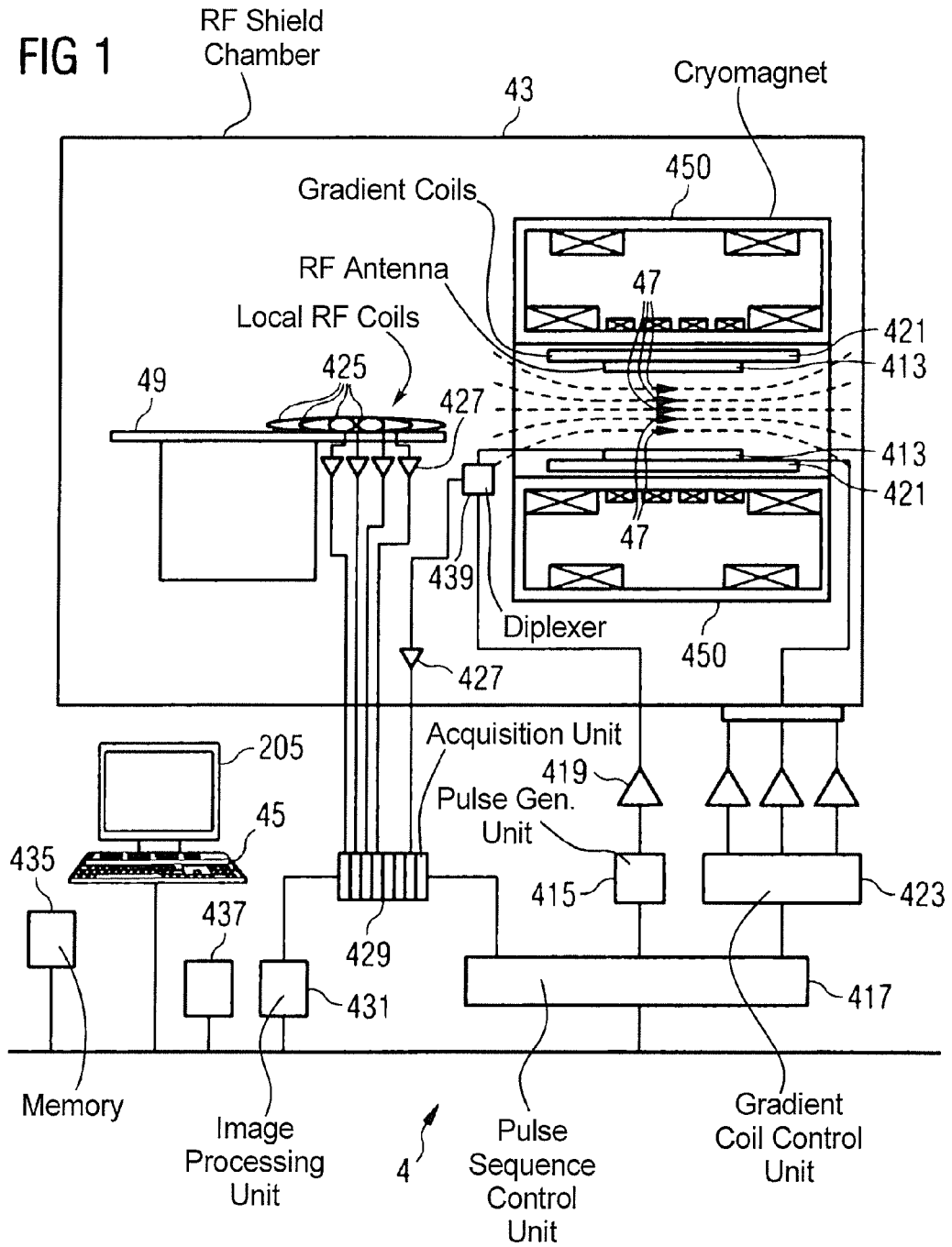
FIG. 1 is a block diagram of an MR scanner.

FIG. 1 shows the principle design of an MR scanner 4 with its essential components. In order to examine a body by means of MR imaging, various temporally variable magnetic fields that are tuned exactly to one another in terms of their temporal and spatial characteristics are radiated towards the body, and this leads to a resonant response of the nuclear spins to the radiated radio-frequency (RF) energy.

In a measurement chamber 3 shielded against radio-frequencies, a magnet 450 (for example typically a superconducting magnet) is provided that is cooled by liquid coolant. The magnet 450 with a cylindrical opening generates a static basic magnetic field 47 that is typically in the range from 0.1 Tesla to 3 Tesla or more in field strength. The basic magnetic field 47 has a high homogeneity, typically in a range of a few ppm for a volume of (for example) 15 cm diameter. A body or a body part to be examined (not shown in FIG. 1) is borne on a patient bed 49 and positioned in a homogeneous region of the basic magnetic field 47.

A resonant response of the spin system occurs by the RF excitation. It is convenient to realize the RF excitation by RF pulses. Such RF pulses can serve to excite the nuclear spin system and/or to refocus the nuclear spin system, as already mentioned.

The excitation of the nuclear spins in the human body, i.e. normally of the protons in the human body, ensues by magnetic RF pulses that are radiated by a radio-frequency antenna (shown in FIG. 1 as a body coil 413). Naturally, the MR examination of nuclei other than the protons (for example lithium or sulfur) is also possible.

As an alternative to the use of the body coil 413 it is also possible to use special excitation coils or radio-frequency antennas adapted to the anatomy, for instance head coils. The RF excitation pulses required for excitation are generated by a pulse generation unit 415 that is controlled by a pulse frequency control unit 417. After an amplification by a radio-frequency amplifier 410, the RF excitation pulses are conducted to the radio-frequency antenna.

The RF system shown in FIG. 1 is merely schematically indicated. More than one pulse generation unit 415, more than one radio-frequency amplifier 419 and multiple radio-frequency antennas are possibly used in an MR scanner or additional modules. In particular, it is possible to use whole groups of antennas, whereby an improvement of a signal-to-noise ratio can be achieved on the one hand and/or noise effects are dominated by properties of the sample. Phased arrays as they are known to those skilled in the art are noted briefly as possible antennas in this context.

The MR scanner 4 has gradient coils 421 with which magnetic gradient fields for selective slice excitation and spatial coding of the measurement signal are radiated in a measurement of magnetic gradient fields. The gradient coils 421 are controlled by a gradient coil control unit 423 that, like the pulse generation unit 415, is connected with the pulse frequency control unit 417.

The signal emanating from the excited nuclear spin (thus the response to the resonant excitation) is received by a reception coil (for example the body coil 413 and/or local coils 425), amplified by associated radio-frequency amplifiers 427 and additionally processed and digitized by an acquisition unit 429. As for the transmission coils, it also applies for the local coils 425 for reception that the use of smaller coils adapted to the geometry of the region of the body to be examined (for instance surface coils) is advantageous under the circumstances in order to improve the signal-to-noise ratio.

Since, according to the reciprocity principle, good transmitters also represent good receivers, it is possible to operate a coil as both a transmission coil and a reception coil. In the case of the use of a coil as a transmission and reception coil, however, it is necessary to ensure a correct signal relaying. This normally occurs by a transmission/reception diplexer 439. For example, a circulator is considered as a transmission/reception diplexer.

An image processing unit 431 generates from the measurement data an MR image that is presented to a user via the monitor 205 or is stored in a memory unit 435. A computer 437 and/or a control unit 45 control the individual components of the MR scanner 4. The control unit 45 is fashioned so that the method according to the invention can be implemented with it.

MR images result via a systematic sampling of frequency space (also called k-space). This sampling of k-space is achieved via suitable sequences of gradient pulses and excitation pulses. Measurement sequences 100 provide a method for how k-space should be traversed. They thus establish the k-space trajectory. For the use of MR in everyday clinical situations it is desirable to find optimally efficient k-space trajectories so that diagnostic images can consequently be generated quickly and efficiently. Today there are a number of measurement sequences 100 that use elaborate and complex strategies in order to sample k-space.

In addition to the time efficiency of the measurement sequence 100, the contrast response for a generated image is also relevant. Depending on the selected measurement sequence 100, quickly responding or slowly responding (i.e. relaxing)tissue parts can be excited. This has a decisive influence on the contrast appearing in the MR image. Measurement sequences 100 are thus likewise to be adapted for the respective selected protocol (i.e. the selected clinical examination) so that a maximum information gain can be achieved for the physician. For example, this applies for the assessment of a cancerous tissue variation that a physician would like to deal with. Measurement sequences 100 for an MR scanner 4 are composed of a series of time slices 10 that result from the physical properties of the nuclear spins and the respective tissue.

FIG. 2 shows an example of a simple measurement sequence 100 of what is known as the spin echo sequence. The temporal progression of a spin echo sequence is shown in FIG. 2. This diagram depicts the temporal progression of the activity in the RF circuit. Moreover, shown below this are the activities of three gradient systems $G_S$ (generally orthogonal to one another) for the selection of a slice as well as $G_P$ as a phase coding (phase encoding gradient, and moreover as a readout gradient that is activated during the readout of the response signal. For a spin echo sequence, the spin system is initially excited with a 90° pulse, whereby an echo arises in the signal. Finally, after the echo time $T_E$ a spin echo that contains information for one line of an image is generated by a 180° pulse, as shown in FIG. 1. As indicated, the phase encode gradient $G_P$ is run through multiple times and its amplitude is varied from one pass to the next. The slice select gradient remains unchanged across all of these passes; the same applies for the readout gradient.

The individual time slice types are drawn, marked from left to right, in FIG. 2. The spin echo sequence thus initially begins with a time slice of the transmission type (I in the drawing) while the 90° pulse is radiated on the excitation side; following this is a time slice of the warp type to prepare the spin system (II in the drawing). A new time slice of the transmission type with the 180° pulse is next (III in the drawing), followed by an additional warp block (IV in the drawing) and finally the time slice of the reception type in which an echo is received as an RF signal (V in the drawing). The time slice of the transmission type ST with the 180° pulse serves to refocus the nuclear spin system. The sequence repeats after the time slice of the reception type ET. For a spin echo sequence, such a run-through up to TE delivers one line for an MR image in k-space. 128 lines are typically acquired for an image, for example. The image can be presented in position space via a suitable Fourier transformation, and an MR image is obtained.

According to the invention, a measurement sequence 100 is constructed from non-overlapping time slices without pauses between the time slices. Sequence programming today is event-based, wherein gradients and RF pulses are grouped as event blocks. Typically the measurement sequence in FIG. 2 is treated as an event block and passed to the scanner 4. One disadvantage of this treatment is that the real-time behavior of the system can be compromised. Moreover, the mathematical modeling of event groups can be very difficult.

It has proven to be advantageous to represent the flow of time slices that makes up a measurement sequence 100 as blocks that exhibit two different types:
warp blocks W in which only gradients are active, and
non-warp blocks in which RF pulses are emitted and/or data are acquired in connection with gradients.

Non-warp blocks are thus X blocks of the transmission type ST and/or of the reception type ET. In the following these blocks are called X blocks X [sic?] for the sake of simplicity. During the duration of the X block, gradients and the transmission and/or reception activity must interact very exactly in order to achieve correct results. For many measurement sequences the exact interaction is simple to achieve since the gradient remains constant during the transmission and/or reception interval. More complicated measurement sequences (for example VERSE, 2D excitation, spiral trajectory etc.) require an exact switching of the gradients in order to generate k-space trajectories that match the RF pulses or the desired form of the data acquisition. Therefore the exact gradient shapes must be defined during the execution of the X block X.\

From the viewpoint of the sequence programmer it is important that the nuclear spins have a defined phase at the beginning of the X block X. Moreover, it is important that the gradient has a specific value when an X block starts in order to be in the position to execute the required switching during the execution of the X block.

The task of the warp block W is to imprint a specific phase onto the nuclear spins and to achieve a specific gradient value at its end. Here it should be underscored that, from the viewpoint of the sequence programmer, it is insignificant how the warp block W reaches the known gradient values at the start and at the end of the warp block W. This means that the exact gradient shape is not relevant. If it is said that the gradient shapes are relevant, in most cases what is meant is that it is desired to control only the phase of the nuclear spins in a specific manner, and that it is believed that this would be achieved via gradient shapes. The proposed formal description of the measurement sequences receives the freedom in the selection of the gradient shape, wherein only start value and end value of the gradients within the X block are relevant for the modeling of the formal description of the measurement sequence 100 based on the sequence model.

Therefore it appears to very appropriate to associate every X block X with precisely one warp block W that precedes it. This is based on the fact that at least one warp block W is needed in order to manipulate the phase of the nuclear spins and to switch the gradient amplitudes between two X blocks. It is not clear why more than one warp block W should be required between two X blocks. In contrast, the use of more than one warp block W between two X blocks C appears to be an unnecessary limitation for the optimal calculation of the gradient response between two X blocks.

FIG. 3A shows as an example the form of a WX block WX as a series of a warp block W which is followed immediately and without pause by an X block X. Such a unit is also designated in the following of this text as a WX block WX. In the following it should be argued only briefly why the warp block W is not arranged temporally after the X block, and why it is necessary to assemble warp block W and X block X as one unit (as a WX block).

Insofar as it is desired to associate a warp block W with an X block X, it can still be decided whether the warp block W precedes the X block or vice versa.

To execute an X block it is necessary to impress a phase on the spin (and in fact in a predetermined manner) and also to specify an established start amplitude for the gradients. This is not possible after execution of the X block.

To execute a warp block W, the properties of the warp block W must be known. The start and end amplitude of the gradient of the warp block must likewise be known. This applies for a sequence programmer and likewise for the software which should execute the measurement sequence 100. In both cases it is difficult to analyze the future time slices or, respectively, blocks of the measurement sequence 100 in order to discover what the end amplitude of the warp block W for the gradients could be. In the event that it is desired to also sub-divide the measurement sequence 100 into sub-sequences 101, what happens outside the sub-sequence or after execution of the sub-sequence on a global time axis t of the measurement sequence 100 is completely unknown within the sub-sequence 101. By contrast, for a software which executes the measurement sequence 100 in the MR scanner 4 and/or a control unit 45 connected with the MR scanner it is simple to consider past blocks and to determine the end amplitude of the last executed X block X as a start amplitude of the next warp block W. The end amplitude of the warp block W is provided by the start amplitude of the associated X block X.

For the X block itself it is in no way relevant what happens after it; as soon as the X block has ended, everything is finished. The X block X does not need to know what happens in the future.

The basis for manipulation of the gradient moments after the X blocks X is to initiate processes such as the rewinding of the gradient moments or spoiling that affects X blocks X in the future. Rewinding and spoiling are known to those skilled in the art. Rewinding and spoiling can be achieved simply in that the moments that are required are stored, and in that it is ensured that these are ended by the respective next warp block W.

In summary, it is simple and appropriate to execute the measurement sequence 100 in units of a warp block W followed immediately by an X block X, without this procedure limiting the freedom of the programmer. This means that the programming of measurement sequences 100 is retained using this approach that is characteristic of the sequence model. Therefore the entire measurement sequence 100 can be presented as a stream of X blocks X and their associated warp blocks W. The selection of a unit of warp block W associated with an X block X has turned out to be advantageous in order to specify the minimal information that is necessary in order to describe a measurement sequence 100.

In the following the term "a center of an X block X" is used. For X blocks of the transmission type ST, this center is typically defined by the asymmetry of the RF pulse that is used. For an X block X of the reception type ET, the center is typically defined by the position of the echo within the X block of the reception type ET. The center of an X block X is an important point in time in the determination of sequence times and for calculation of the gradient moments within the measurement sequence 100.

It appears to be sufficient that each X block X possesses only one center. Naturally, the formulation of more than one center per X block X would be possible.

In the sequence model according to the invention, there are three different types of time measurements. These types of time measurements are:

a time duration of an X block X, a sequence time that is measured between the centers of two X blocks X. Examples of such times are the repetition time TR, the echo time TE, the inversion time TI and the echo interval.

moreover, a sequence start time T.30 as a point in time of a center of a respective first block X within a measurement sequence 100.

These individual times are shown in FIG. 3B. The sequence start time T.30 is indicated by the center X of the first X block; an echo time TE reaches from the center of the first X block X to the center of the second X block X. A repetition time TR identifies an additional sequence time at which the measurement sequence 100 is repeated. In order to completely describe the timing of a measurement sequence 100 with these three types of time measurements on the global time axis t, it is necessary that a sequence time ends at each X block X within the measurement sequence 100. This is actually the case for all known measurement sequences 100. In addition to the repetition time TR, the (spin) echo time TE and an inversion time (TI), there is also the echo interval for EPI (Echo Planar Imaging) and turbo-spin echo sequences and the RF interval for binomial pulses as they are used in typical MR scanners 4 today. Therefore this is not new information that the sequence programmer must specify; at most the necessary form of the presentation changes. In contrast to this, an exception is to be made for the first of the X blocks X within the measurement sequence 100. For the first X block X, the time of its occurrence must be known in the form of a sequence start time T.30. This is specified for the center of the first X block X. Insofar as these time measurements and/or points in time are known for all X blocks X within the measurement sequence 100, the duration of all warp blocks W within the measurement sequence 100 can be calculated. This calculation can also be completed at run time during the execution of the measurement sequence 100 in an MR scanner 4 and/or in a control unit 45 connected with the MR scanner 4.

It is noted that the selection of the time measurements between X blocks is arbitrary. Their time measurements between the individual warp blocks W would likewise be possible. However, the elegant translation into sequence times would then no longer be possible as simply.

With the representation of a measurement sequence 100 in the framework of the sequence model as a series of warp blocks W and X blocks X (wherein these are combined as WX blocks WX), for each echo a path for its creation can be specified. FIG. 3C shows series of warp blocks W and X blocks X for known sequences. Shown in the uppermost line is the series for a gradient echo sequence GRE; under this are located depictions of the echo planar imaging sequence EPI, for a spin echo sequence SE as it was already shown in FIG. 2, a combination of spin echo and EPI measurements SE-EPI, and TSE for a turbo-spin echo sequence. For each of the X blocks X of the transmission type ST and/or reception type ET it is specified whether an echo is generated and which series of X blocks X of the transmission type ST and/or reception type ET has contributed to the creation of the echo. "E" at the corresponding label thereby stands for an excitation; in contrast to this, "R" stands for the refocusing. In this context it is again noted that there are also hybrid forms made up of excitation pulse and refocusing pulse. Stimulated echoes are also important in this context.

More than one echo specification per X block X of the reception type ET are possible via stimulated echoes. For this it is necessary to set up the gradient moment equations for each of the echo specifications. The sequence model—based on the combination of warp block W and X block X into a unit as a WX block WX—allows the setup of the sequence equations for each of the warp blocks W and their associated X block X.

An index i can be associated with each of these WX blocks WX.

The duration of a warp block W is $T_{w,i}$.

The duration of the X block X before its center is $T_{xs,i}$.

The duration of the X block X after its center is $T_{xe,i}$.

The gradient amplitude at the beginning of the X block X is $G_{s,i}$.

The gradient amplitude at the end of an X block X is $G_{e,i}$.

The gradient moment of the order h of the warp block W is $M_{h,w,i}$.

The moment of the h-th order of the X block X before its center is $M_{h,xs,i}$.

The moment of the h-th order of the X block after its center is $M_{h,xe,i}$.

An echo specification $\xi$ which represents the path for echo creation as a vector is associated with each X block X that is not purely of the transmission type ST.

An X block X of the (not necessarily a pure X block X) of the reception type ET has a zeroth gradient moment $M_{O,Echo,i}$ that must be realized at its center.

After the gradient moment equations are specified, the paths for echo creation for each X block X that is of the reception type ET can also be specified. A set of indices $I_R$ must thus be generated which contains the indices i of all of those WX blocks WX for which an echo specification $\xi$ exists. For a specific index k from the set of indices $I_R$ for which an echo specification exists, the stream of WX blocks WX must be analyzed in reverse up to that WX block which contains the RF excitation pulse of the echo specification. The index for this WX block WX for excitation with $k_{ex}$, wherein $k_{ex} < k$, is the index of the echo. A vector s is also generated for which it applies that $N_s = k - k_{ex}$, which contains the elements $s_i$ with $i \in \{0, \ldots, N_s-1\}$ and specifies which coefficients are to be used for the calculation of the moments within the gradient moment equation.

Figure 4:
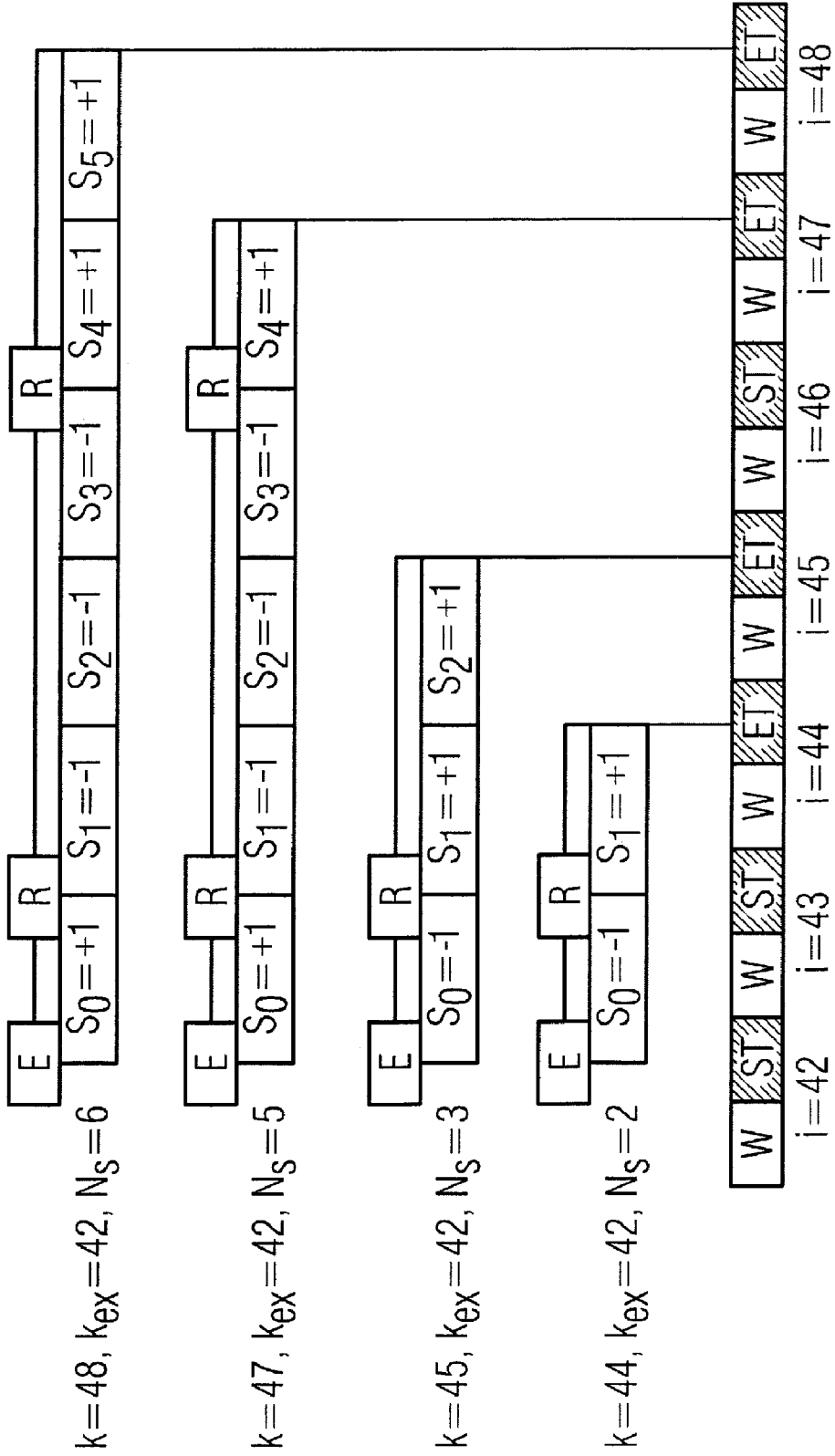
FIG. 4 shows a path for echo creation for a measurement sequence from the directed graphs.

A graphical representation of such an analysis of the echo specification is shown by way of example for a turbo-gradient spin echo sequence TGSE in the illustration of FIG. 4. The required information for calculation of the gradient moments can be determined from this path for echo creation (i.e. the echo specification). This determination can in fact proceed automatically. Possibly stimulated echoes are likewise to be taken into account in a very closely corresponding manner.

Through association of the variables as listed in the above list, moment and sequence equations for each of the X blocks X can be specified. The gradient moment of the zeroth order in the center of an X block X with index h is provided by $$M_{0,k} = \sum_{i=0}^{N_s} S_i(M_{0,xe,k_{ex}+i} + M_{0,w,k_{ex}+i+1} + M_{0,xs,k_{ex}+i+1})$$

The moment satisfies the following equation:

$$M_{O,k} = M_{OEcho,k}$$

The moment of the first order at the center of the X block X with the index k is $M_{i,k}$. This gradient moment of the first order to can calculated according to the following with regard to the distance $\delta$ to the center of the RF pulse:

$$M_{1,k} = \sum_{i=0}^{N_s} S_i m_{1,i}$$

with $$m_{1,i} = M_{1,xe,k_{ex}+i} + M_{1,w^*,k_{ex}+i+1} + M_{1,xs,k_{ex}+i+1}$$
$$+ M_{0,xe,k_{ex}+i}(T_{s,i})$$
$$+ M_{0,w,k_{ex}+i+1}(T_{s,i} + T_{xe,k_{ex}+i})$$
$$+ M_{0,xs,k_{ex}+i+1}(T_{s,i} + T_{xe,k_{ex}+i} + T_{w,k_{ex}+i+1})$$

and $$T_{s,i} = \delta + \sum_{j<i} (T_{xe,k_{ex}+j} + T_{w,k_{ex}+j+1} + T_{xs,k_{ex}+j+1})$$

Insofar as a velocity coding $V_k$ for an X block X with index h is desired, it is sufficient to known a unit vector $e_v$ in the direction of the desired velocity. As soon as the unit vector is provided, the velocity coding of the X block k can be specified directly via the gradient moment of the first order $M_{1,k}$ since $$V \alpha e_v \cdot M_{1,k}$$

Such a velocity coding is in particular of interest for the examination of signal portions that move with the velocity $V_k$. Such signal portions can either be isolated or suppressed. It is noted that this diffusion weighting is already possible without knowing the details of the individual X blocks. Rather, this information can already be achieved from sufficient "bookkeeping" across all WX blocks WX.

Corresponding equations can be formulated for higher gradient moments and diffusion weighting. A diffusion value would then have to be associated with the X blocks X.

The sequence equations for each sequence time measurement can be specified in a very analogous manner within the measurement sequence 100. Insofar as the time measurement is (for example) a sequence time whose measurement begins with an X block X with index $k_b$ and ends at a further X block X with index $k_e > k_b$, it applies for this sequence time that $$T = T_{xe,k_b} - T_{xe,k_e} + \sum_{i=k_b+1}^{k_e} (T_{w,i} + T_{xs,i} + T_{xe,i})$$

Today a measurement sequence 100 is described by the incorporation of what is known as a "sequence core" into a loop structure in which the sequence core is executed repeatedly. The sequence core implements the basic scan techniques, for instance gradient echo (GE), turbo-spin echo (TSE), true FISP (TRUFI), echo planar imaging (EPI) etc. The loop structure repeatedly invokes the sequence core in a fully defined manner for all raw data lines in order to generate from these all MR images which should be measured by the measurement sequence 100. A "protocol" is the measurement sequence 100 together with a set of specific parameters for the measurement sequence 100, for instance the field of view (FOV), the resolution, the echo time, etc. An examination normally is composed of a number of such protocols that are executed in series. A measurement sequence 100 consists of at least a single X block X with its associated warp block W, as shown in FIG. 3A. A sequence can likewise represent a complete examination of a patient. A measurement sequence 100 thus moves between these two extremes. In order to register the structure of a measurement sequence 100, it is recommended to sub-divide the entire stream of WX blocks WX into modules: This approach has proven to be very effective.

The entire stream of WX blocks WX typically consists of many different MR measurements, for example the acquisition of multiple slices that are acquired simultaneously. The acquisition of a single slice could be described independently, for example, and be viewed as an independent module. Multiple instances of this module that are executed in an interleaved manner so that the timing of the different modules does not overlap would then be necessary for examination, i.e. for the acquisition of multiple slices. Such a module can be designated as a "reasonable sub-set of WX blocks WX" or as a sub-sequence 101.

Within a sub-sequence 101, regions are provided for which the sequence programmer explicitly allows that other sub-sequences 101 to implement tasks in the hardware of the MR scanner 4 without interfering with the measurement. The reasons for this are the interleaving of slices in multi-slice measurements and the inversion measurement of individual slices that today allow that something is executed even between the inversion pulse and the excitation pulse. Such a region within a sub-sequence 101 is designated as a pause P. Because an X block X and its associated warp block W are executed as a unit, such a pause P can occur only after an X block X and before a warp block W. The pauses P sub-divide the sub-sequence 101 into indivisible superblocks 102 that may not be interrupted.

A sub-sequence 101 comprises a start time T.30 that specifies where on the global time axis t the first block X block X of the sub-sequence 101 emerges.

FIG. 5A shows a sub-sequence 101 embedded into a stream of WX blocks WX. The sequence times via which the individual X blocks X of the sub-sequence 101 are connected with one another are likewise shown.

FIG. 5B shows the same sub-sequence as in FIG. 5A, however without the remaining WX blocks WX. Instead of this, the indivisible superblocks 102 of the sub-sequence 101 are shown that are connected via pauses P.

Interestingly, the two conditions—each sub-sequence 101 has global start time T.30 and the superblocks 102 of the sub-sequence 101 are connected via sequence time measurements for each of the sub-sequences 101—are sufficient in order to correctly execute a set of sub-sequences 101. This means that the execution of the set of sub-sequences 101 functions without calculating every additional loop structure and without calculating the necessity of fill times.

The concept of the sub-sequences 101 allows the construction of measurement sequences 100 using instances of arbitrary sub-sequences 101. Every instance of a sub-sequence 101 has a pattern, i.e. a characteristic on the global time axis t. In order to achieve short measurement times or in order to achieve a special physical effect (for example the regional saturation of the fat signal), instances of sub-sequences 101 must be interleaved on the time axis t. The fingerprint of a sub-sequence 101 on the time axis t is provided by the number of superblocks 102 within the sub-sequence 101 and the duration of each superblock 102. Therefore the interleaving of the sub-sequences 101 depends on the fingerprints or, respectively, the characteristics of all sub-sequences 101 on the global time axis t.

Due to long-term hardware and patient limitations, for example the switching cycles RF of power amplifiers as well as tissue-specific absorption rates (sensor arrangement), the length of any one warp block W and/or X block X depends primarily on what has happened before a warp block W on the global time axis t. In other words, long-term limitations describe those limitations that must be complied with over the entire course of the measurement sequence 100.

The time axis characteristic of a sub-sequence 101 depends on the interleaving of the sub-sequences 101. In order to thus correctly describe and calculate the sequence timing, it is necessary to consider the timing problem of the sub-sequence 101 and the problem of the sub-sequence interleaving together. It is possible to specify a complete problem description, at least insofar as the number of sub-sequences 101 is known in addition to the number of WX blocks WX and superblocks 102 for each of the sub-sequences 101. Unfortunately, this problem is generally not solvable insofar as the computing power that is presently available is taken into account. What makes this problem even more difficult is the fact that the determined timing values T.i for the individual WX blocks WX must be fitted to the time schedule of a magnetic resonance scanner 4. Insofar as this requirement is already formulated as a boundary condition for the solving of the one problem, a numerical solution to timing problem becomes nearly impossible.

Refer in this context to DE 10 2008 044 827.3 by the applicant, which discloses a solution for the adaptation of the time schedules within a measurement sequence 100 to the time schedule of a magnetic resonance scanner 4. Heretofore, a sequence model has been used that describes numerous aspects of a measurement sequence 100, for example the timing definition, meaning the definition of the relative temporal progression within the measurement sequence 100, the echo specification, gradient moments of the zeroth order, first order and higher orders. The sequence model allows MR measurements from sub-sequences 101 or sub-sequence modules to be acquired that can act as a basis of an application-specific programming language for sub-sequences 101, and therefore also for measurement sequences 100.

The present invention provides an efficient method for description and generation of sub-sequence modules. This is achieved by means of a formalized description. The formalized description, which can additionally be written simply and concisely, ultimately serves to parameterize a complete MR measurement from the formalized description, and therefore to optimally completely parameterize the entire measurement sequence 100. Therefore an optimal mixture of formalism and flexibility can be achieved. Earlier scanners had a formalism for description of the measurement sequence 100 but offered only very little flexibility to the sequence programmer. Approaches to description that offered the sequence programmer great flexibility in the programming followed these. However, this flexibility was purchased with a high programmer effort.

The formal description of a measurement sequence 100 of a directed graph G can also be understood in the sense of an automaton or a finite state machine. The described sequence model allows the sequence programmer to write the specification of sub-sequences 101. These sub-sequences 101 are used to generate software libraries which execute the sub-sequence 101 and produce sequence-dependent plug-ins with the sequence data, i.e. the sequence description. The sequence-dependent execution plug-ins can be thought of as, for example, a C++ class which (when populated with values) describes a measurement sequence 100 so that it can be executed in an MR scanner 4 and/or in a control unit 45 connected with the MR scanner 4. These execution plug-ins provide the functionality for execution of the sequence on different hardware and software platforms to design the measurement sequence 100 [sic?]. The formal description also serves as input values for numerous solvers. Any function extension can be formulated and used as an additional execution plug-in without having to change the sequence descriptions.

A measurement sequence 100 of the gradient echo (GRE) type is shown in FIG. 5B. The goal of the formalized description of a measurement sequence is therefore to find an efficient way to specify all WX blocks WX without having to explicitly specify every WX block. Moreover, the description of the sub-sequence 101 should exist in a parameterized form.

In the formal description according to the invention of a measurement sequence based on the sequence model, a gradient echo-like GRE sub-sequence can be represented as a directed graph G as it is shown in FIG. 6. For a practical measurement as it is used clinically, 65536 lines of raw data are necessary for a 3D experiment whose representation on the global time axis t by means of individual WX blocks WX is unacceptably long. In contrast to this, the parameterized, graphical representation in the form of the directed graph G the same; just as many k-space lines are acquired.

This directed graph G and the programming language or, respectively, the data model connected with this are explained in the following using the gradient echo sequence GRE as a possible example of a measurement sequence 100 that consists of a single sub-sequence 101. This formal description of the directed graph G can be completely and automatically translated into a machine-readable format, as is described further below.

The directed graph G for a measurement sequence 100 (and therefore also for a sub-sequence 101) reproduces the relative connections (for example of a temporal type) among the individual WX blocks WX and can be completely parameterized, i.e. populated with concrete values. The basic principle of the sequence model is the fact that it is based on blocks of the group warp block W, X block X, pause P. The directed graph G of a sub-sequence 102 comprises nodes, edges Ka and properties of the edges for workflow control of the directed graph G. The nodes comprise the group consisting of X block X, entrance point I and exit point O. Entrance point I and exit point O assume a special position in a certain sense since they mark the start of the directed graph G as entrance point I and the end of the directed graph G as exit point O. In the selected graphical representation of the directed graph in FIG. 6, the entrance point I is therefore depicted as a triangle pointing downward while the exit point O is depicted as a triangle pointing upward. As soon as a directed graph G has ended, the process can jump to a further directed graph G of a sub-sequence 102 or of a measurement sequence 100. The remaining nodes of a directed graph (that are thus not entrance point I and/or exit point O) are provided by the X blocks X. These are represented by ellipses in FIG. 6 and in the following. The nodes of a directed graph are connected via edges Ka. The edges Ka are also provided with properties for workflow control of the directed graph G. The edges Ka likewise represent transitions as they are known from state models of an automaton or from graph theory. The properties of the edges Ka for workflow control reproduce characteristic properties of the measurement sequence 100. These properties of the edges Ka for workflow control are provided by the group consisting of: a warp block W, a time measurement, a pause B and a path control P [sic; this appears to be changing the reference character for pause from "P" to "B" and reassigning "P" to path control]. Only very specific transitions are allowed for a directed graph G that should parameterize a measurement sequence 100. These permitted transitions are:

A transition from the entrance point I via a path control P to an X block X, as well as a transition from an X block X via a path control P to the exit point O. A transition from an X block X via a path control P to a warp block W and from there to an X block is also permitted. Furthermore, a transition from an X block X via a path control P and a pause B to a warp block W, and from there to an X block X, and finally a transition from an X block via a time measurement to an X block X.

The edges Ka of the directed graph G are provided by lines. Time measurements in the directed graph G are depicted by mean of round circles in which the respective sequence time to be measured are specified, for example the echo time TE or the repetition time TR.

Path controls P are to be understood in the sense of queries that must be satisfied so that an edge Ka of the directed graph G can be entered.

Warp blocks W (that are represented as a rectangle in the directed graphs as in FIG. 6) belong to the properties of the edges Ka for workflow control. Furthermore, the time measurement properties of the directed graph G for workflow control are represented as circles in the directed graph.

The principle for execution of a measurement sequence 100 is the execution of a WX block, the use of the path controls P in order to find out which WX block WX is to be executed next, and to repeat this until the exit point O of the measurement sequence 100 is reached.

Sequence times within a directed graph G (for example the echo time TE or the repetition time TR in FIG. 6) are used in order to calculate the length of the warp blocks at run time. All elements of the directed graph G (thus nodes, edges Ka, properties of the edges Ka for workflow control) represent a very specific functionality of the measurement sequence 100 or, respectively, the sub-sequence 101.

The warp blocks W and the WX blocks WX represent a control structure for all warp blocks W and X blocks X within a measurement sequence 100 that can be generated from the directed graph as concrete warp blocks W, or X blocks X. In other words, the warp blocks and X blocks X as they are represented in the directed graph G establish the relation of the two types of blocks relative to one another without determining their specific duration. In order to generate time slices that can be executed in a magnetic resonance scanner 4 from the warp blocks W and X blocks X, it is necessary to establish their duration. Therefore every X block is to be provided with nodes with a time index function. The time index function allows the grouping of X blocks X to be combined within a measurement sequence 100.

Upon "unrolling" the directed graph G, a time variable $T_{xs,i}$ and $T_{xe,i}$ is created for every used instance of an X block X of the directed graph G. The time index function is used in order to establish whether and how the values of these time variables differ from one another. For example, it can therefore be established that all time variables that are associated with the X block X should have identical values. Alternatively, it may be allowable (for example) for all time variables that are associated with the X block X have different values. Furthermore, it can be established (for example) that, although the time duration of a refocusing pulse within a turbo-spin echo sequence changes with the echo number, it does not change with the echo train number. Therefore measurement sequences 100, which today can be realized only with a significant programming effort, can now be realized in the simplest manner, possibly in combination with the boundary conditions 2500 for the solver 2000. Such measurement sequences are, for example, VET measurement sequences ("variable encoding time") or measurement sequences 100 with variable readout bandwidths.

The example shown in FIG. 4 of a gradient echo sequence GRE contains an X block X of the transmission type ST for excitation (designated with "Excite") and an X block X of the reception type ET that is designated with "GradEcho" in the drawings. The node "Excite" can be reached via the warp block W, which in the drawings is "Excite 0", and from the sequence entrance point I and via the warp block W to the nth echo excitation (in the drawings "ToExciteN" from gradient echo X block "GradEcho"). In contrast to this, the X block "GradEcho" for echo generation can be reached exclusively from the excitation pulse "Excite" via the warp block to the gradient echo "ToGradEcho".

As already mentioned, the measurement of sequence times is defined between X blocks X. The name of the sequence time is thereby part of the description. Such a name can be the echo time TE, the repetition time TR or the inversion time TI, for example. Sufficient sequence times must exist in order to be able to define the length of the warp blocks W. At least one measurement of a sequence time must end at every X block, with the exception of the first X block X within a sub-sequence 101 whose global time t is defined by a sequence start time T.30. Every sequence time measurement is also associated with three functionalities that are not apparent from the graphical representation of the directed graphs G. These are first a condition of the sequence time measurement that indicates whether the measurement of the sequence time is started at a specific X block X on the global time axis t. An additional condition for measurement of a sequence time can indicate whether the measurement of the sequence time is to be stopped at the specific X block X on the global time axis t. Lastly, a time index function that allows the sequence programmer to associate an index with a given sequence time can be used. For the example shown in FIG. 6 for a gradient echo sub-sequence GRE, the echo time TE and the repetition time TR are present as sequence times. The echo time TE is always measured from the excitation pulse "Excite" to the gradient echo "GradEcho". In contrast to this, TR is measured from one excitation pulse "Excite" to the next. The measurement of the repetition time TR may not be stopped for the first excitation pulse "Excite". The measurement of the repetition time TR may also not be started for the last of the excitation pulses "Excite".

The entrance point I simply designates the introduction, i.e. the beginning of the sub-sequence 102 and therefore of the measurement sequence 100. In contrast to this, the exit point O indicates the end of the sub-sequence 101 or, respectively, of the measurement sequence 100. With an optional pause B, the sequence programmer has the possibility to explicitly permit the interleaving with other sub-sequences 101. A pause B is located before every excitation pulse "Excite" in the example of FIG. 6, with the exception of the first excitation pulse "Excite". For a true FISP measurement sequence TRUFI as it is known to those skilled in the art, such a pause B is not present because the required quasi-stationary state (also called "steady state") would thereby be destroyed. Therefore the pause B for a TRUFI measurement sequence is absent.

The path controls P play a very important role within the directed graph G. A path control P defines the sequence in which WX blocks WX are executed within the sub-sequence 101. Every X block X has at least one successor. After a WX block WX has been executed, the path controls P of all possible successors are queried in an arbitrary order as to which of the possible successors is the actual successor. Only one of the queried path controls P may respond to this question with yes. With the path controls P, sub-sequence indices are checked and modified. Although all other functionalities are local, the workflow control within the sub-sequence 101 requires a global knowledge that is applicable for the entire sub-sequence 101. Therefore in general all path controls P must cooperate within the sub-sequence 101 in order to ensure the correct sequence of WX blocks WX within the sub-sequence 101. Therefore the formulation of a group of path controls P appears to be the most difficult task for a sequence programmer.

It is noted that the depiction of the measurement sequence 100 as a directed graph G can show interleaved loop structures without any trouble. In contrast to classical formulation of interleaved loop structures, the presentation as a directed graph G is made more productive by means of the path controls P. Not all of the control structures as they can be depicted as a directed graph G can be formulated by means of interleaved loop structures within this formal description of a measurement sequence 100. For example, for the example shown in FIG. 6 the path control that is always to be satisfied is designated with "Always" in the drawings, meaning a path control that ensures that a gradient echo "GradEcho" is always acquired after an excitation pulse "Excite". The shown example of a gradient echo-like sequence GRE acquires an additional gradient echo "Grad Echo" as long as all gradient echoes "GradEcho" have not yet been acquired. As soon as the last gradient echo "Grad Echo" is acquired, the sub-sequence ends at the path control P to the ending (designated with "Finished" in the directed graph G).

A re-sorting functionality can also be executed in a sub-sequence 102 or a measurement sequence 100. This possible functionality of the re-sorting is not shown in the graphical representation of the directed graph G. The task of the re-sorting functionality is the calculation of sub-sequence indices from a predetermined set of sub-sequence indices. This re-sorting functionality is executed in arbitrary order before every warp block W. In order to avoid unnecessary complications, it is reasonable to ensure that the output indices of the re-sorting functionality are not those indices which are exclusively modified by the path controls P. For the example of the gradient echo-like sequence GRE shown in FIG. 6, the k-space line and the partition index are calculated from the index of the gradient echo. For a gradient echo within a gradient echo sequence GRE for which (for example) five gradient echoes are generated in one pass (thus the echo train is five echoes long), it must be designated (indicated) which group of k-space lines is acquired for each of these echoes. Which k-space line is to be coded can then be determined from the number of the echoes. These types of re-sortings are well known to those skilled in the art. It is likewise known how a possible accentuation of edges and the like that result directly from the selected distribution of the individual k-space lines in the different echoes is to be executed.

In order to show the interaction of the individual elements of a directed graph G, the acquisition of a k-space line is now discussed step by step for a gradient echo-like sequence GRE as it is shown as a directed graph G in FIG. 6. The current position in the directed graph G is thereby characterized by a bold depiction of the respective element. The respective position on the global time axis t is likewise found in following Figures.

FIG. 7A shows the entrance into the directed graph G at the entrance point I. In this Step the sequence start time T.30 for the sub-sequence 101 is initially established on the global time axis t.

FIG. 7B is one Step further in the directed graph G and reaches the warp block "ToExcite0" after the path control "Always" that is always to be satisfied. This warp block "ToExcite0" requires the first excitation pulse "Excite".

In FIG. 7C the first excitation pulse "Excite" is reached, and the excitation of the spin system for the first k-space line ensues.

FIG. 7D shows that the sequence time measurement of the echo time TE is started upon reaching the first excitation pulse "Excite". This proceeds from the "Excite" block and is designated in bold in the lower part of the image in the directed graph G.

FIG. 7E shows that an additional measurement of a sequence time (namely that of the repetition time TR) is also started upon reaching the excitation block "Excite". All time measurements that proceed from the excitation block "Excite" are therefore started.

In FIG. 7F the path control "Always" that is always to be satisfied enforces the progression in the directed graph G to the warp block "ToGradEcho". The path control "Always" that is always to be satisfied is therefore shown in bold in the directed graph G. This check of the path control P to locate the successor of the X block "Excite" is indicated by a question mark on the global time axis t in the upper part of the image. A gradient echo "GradEcho" after the excitation by the excitation block "Excite" is thus always enforced. The measurement of the sequence time TE is stopped upon reaching the gradient echo "GradEcho", thus the X block of the reception type for acquisition of the gradient echo "GradEcho". This is apparent in FIG. 7G.

FIG. 7H furthermore shows that a warp block "ToGradEcho" that precedes a gradient echo "GradEcho" is always executed after the path control "Always" that is always to be satisfied.

In FIG. 7I the X block "GradEcho" at which a gradient echo is acquired is executed. This is recognizable both in the directed graph G and on the global time axis t. After execution of the X block X, the directed graph G reaches two path controls P that are effectively parallel to one another. One of these path controls P indicates the end of the sub-sequence 101 (the path control "Finished"), and the other indicates the further acquisition of k-space lines. This path control is identified with "AnotherScan" in the directed graph G. In the event that a further k-space line is to be acquired, a pause B initially follows, followed in turn by the warp block "ToExciteN", wherein N identifies that this warp block precedes the nth excitation. Only when all k-space lines are scanned (thus all gradient echoes "GradEcho" have been acquired) is the sub-sequence 101 ended and the path control "Finished" to the end of the sub-sequence 101. The exit point O in the directed graph G is thereupon reached. As soon as the excitation pulse "Excite" for the next k-space line is reached, the sequence time measurement for repetition time TR is stopped. This occurs in a manner very analogous to the measurement of the echo time TE. However, the repetition time TR connects two superblocks 102 within a sub-sequence 101 (and therefore a measurement sequence 100), as is apparent from the temporal progression in the upper part of the images.

It is in particular noted that the use of the formal or, respectively, formalized description that can be depicted in a directed graph G for a measurement sequence 100 that should be executed in an MR scanner 4 allows a parameterization of the measurement sequence 100 to be extracted from the directed graph G, which measurement sequence 100 has already been completely parameterized except for a set of parameters 1100 to be determined.

As shown in detail above in connection with FIG. 7, the relative connection of the individual WX blocks WX within a sub-sequence 101 (and therefore within a measurement sequence 100) can be determined from the directed graph G. Moreover, the corresponding directed graph G of a sub-sequence 101 or, respectively, a measurement sequence 100 represents the minimal set of necessary information in order to completely parameterize the sub-sequence 101 or the measurement sequence 100 except for a set of parameters 1100 to be determined. In particular, an additional loop structure is no longer necessary in order to depict or "roll out" a measurement sequence 100 represented as a directed graph G on the global time axis t.

Therefore, the sequence model that represents the measurement sequences 100 (and therefore also the representation of the sub-sequences 102) forms the basis for a user-specific programming language for sequence programmers. The specification of the measurement sequence 100 that is provided in the directed graphs G embodies the minimum necessary information that the sequence programmer must provide. This sequence description can be used in a wholly conventional manner by a build system to generate software. A "build system" is a system that integrates libraries into source code files and generates an executable software. Moreover, it is possible that sequence-independent software modules use the data stream of the measurement sequence 100 represented as a directed graph G as input data. It is thus possible to analyze this developer station in various ways.

A solver 2000 may be used in this context to determine the structure of the measurement sequence 100 from the directed graph G and then, for example, to solve the timing problem for the measurement sequence under consideration of the generated sequence equations and determines permissible or suitable timing values T.i. Solvers 2000 are discussed in more detail in the following. It is also possible for new measurement sequences 100 to be directly formulated as a directed graph G. Moreover, an external software module can import the specification of a directed graph G and present this, or calculate phantom images for different timing values T.i. and contrast specifications in order to facilitate the selection of the suitable timing values T.i and their parameters for a user of the MR scanner 4. Sequence-independent software modules (for example a solver 2000) can implement a given directed graph G on the global time axis t (as shown in FIG. 7) and solve the entire timing problem for the directed graph G by means of the sequence equations provided from the directed graph G. This solution can be the respective time durations for all warp blocks W and all X blocks X. The time durations of the warp blocks W implicitly result from the time durations of the X blocks. The solver 2000 can thereupon enter the determined timing values T.i into the respective blocks at the suitable points and thereupon roll up the directed graph G again. Therefore all properties of the directed graph G are now specified. This means that the set of parameters 1100 that are to be determined, which initially were not known from the generic directed graph G, are now populated with concrete values.

In connection with measurement sequences 100 that should be executed in an MR scanner 4, the solver 2000 can also be described according to the following: the solver 2000 is in general a software module that determines all parameters for a MR measurement from a fully defined set of input values. Such a set of fully defined input values is provided according to the invention via the formalized description of the measurement sequence 100 in the form of a directed graph. From this the timing problem can be generally solved with permissible values for the set of parameters 1100 to be determined, wherein the parameters 1100 that are still to be determined are populated with concrete values. These concrete values are determined by the solver 2000. The solver 2000 can thereby additionally taken into account boundary conditions 2500 that are to be satisfied for execution of the measurement sequence 100 in the MR scanner 4. In particular, the measurement sequence 100 is thereby to be completely populated by the solver 2000 with permissible values. The description or measurement sequence specification can now be translated automatically into an arbitrary programming language. This programming language can then be executable directly in the magnetic resonance scanner, for example, and/or in the control unit 45 connected with the MR scanner 4. The boundary conditions 25000 can comprise the following elements: contrast specifications for the MR image. These normally result from the diagnostic question because, for example, $T_1$ weighting may be prescribed in order to answer specific diagnostic questions. As an alternative, $T_2$ weightings are possible, for example, or a targeted fat suppression in an MR image. These contrast specifications have direct effects on the values that are to be selected for the echo time TE, the repetition time TR, the inversion time TI etc. These facts are known to those skilled in the art. According to the invention, such contrast specifications can be provided to the solver 2000 to be executed and solved as mathematical problems, for instance in the form of a mathematical secondary condition that is to be taken into account in the solution of the timing problem by the solver 2000. In addition to these, image resolution specifications are a further possibility for boundary conditions 2500 that are to be satisfied. For example, anatomical facts from which the necessary image resolution results are among these boundary conditions 2500. For example, in order to examine the prostate of a patient, a very high resolution is required but only in a very small target area. The target area is also designated as a field of view (FOV). Moreover, the position specifications for the slices to be examined are to be complied with. Suitable slices must thus be selected for the examination of the heart.

There are also boundary conditions 2500 that already arise as what are known as hardware limitations from the condition of the hardware of the scanner 4. For example, the maximum power of a power amplifier that supplies the gradient coils with gradient currents as well as necessary cooling capacities in order to keep the MR scanner 4 in operation belong to these hardware limitations. If the MR scanner 4 overheats (for instance due to too little cooling capacity), the measurement sequence 100 is interrupted in the running operation of a supervision module such that it must be started over from the beginning. Solely for economic reasons such an interruption of the MR measurements is not desirable since down times arise in which no patient can be examined. Moreover, the risk exists that parts of the hardware of the MR scanner 4 are damaged. An additional possible boundary condition 2500 is the specification that the measurement time that is required in order to execute a measurement sequence 100 should be minimized. This is economically motivated on the one hand since a higher throughput of patients per time unit more quickly amortizes the costs of the MR scanner. Moreover, there are also examinations that mandate a maximum measurement time. For example for measurements in which the patient holds his or her breath. Furthermore, there is a series of patient safety regulations that must also be complied with over the entire course of the measurement sequence. For example, a maximum edge steepness of the gradients arises (i.e., must not be exceeded) from such regulations for protection of the patient from injury or harm. An additional patient safety regulation can also be that the transmitted RF power does not exceed a maximum value. If the radiated RF power is too high, a patient can be burned (as already discussed above). Compliance with these limit values can be realized in practice using, for example, an account model that designates power that would be administered to the patient under the proposed conditions. Such methods are known to those skilled in the art and need not be explained in detail here.

The method according to the invention for formal description of a measurement sequence 100 that can be executed in an MR scanner 4, like the method according to the invention for automatic generation of a measurement sequence 100 for execution in an MR scanner that precedes the formal description of a measurement sequence 100 as described in connection with this disclosure, significantly facilitates the work of the sequence programmer. The administration of the necessary parameters in order to completely describe the measurement sequence 100 is significantly simplified since a majority of the parameters defining the measurement sequence 100 can be automatically determined from the directed graph G. Moreover, all necessary parameters are known with the set of parameters 1100 to be determined, at least as placeholders. This means that they are known without a concrete (specific) value being established. The programmer thus no longer needs to care about the number of parameters for a measurement sequence 100 in the everyday clinical setting. The determination of permissible values for the set of parameters 1100 to be determined can then be conducted by the solver 2000. The solver 2000 determines the parameters 1100 to be determined from the given parameters and their correlations (as they are formally described in the directed graph G) and populates these with permissible values. As soon as all parameters have been described, it is naturally possible to automatically translate this complete specification of the measurement sequence 100. The determination of permissible parameter values was previously a laborious process. The user proposes a plurality of parameter values for execution of the measurement sequence. This input by the user has previously been checked by an inspection module; hardware limitations and/or gradient limitations have been checked in particular. In the event that problems thereby arose, the user of the MR scanner was notified of this via a window or a control element of the user interface 3000 of the MR scanner 4. For example, this can occur via the monitor 205. An intervention by the user was then necessary; this was typically often necessary for a new measurement sequence 100. Inasmuch the determination of permissible values in interaction with the user of the magnetic resonance scanner was sometimes very t-c and tedious. Insofar as the two methods according to the invention are used, the effort for the user is significantly reduced. The set of parameters 1100 to be determined is small. These values are typically what are known as high level parameters, for instance the echo time TE, the repetition time TR and the like. The parameters to be provided by the user are those that are to be intuitively handled by him. They are finally directly linked with contrast properties of the MR image.

Figure 8:
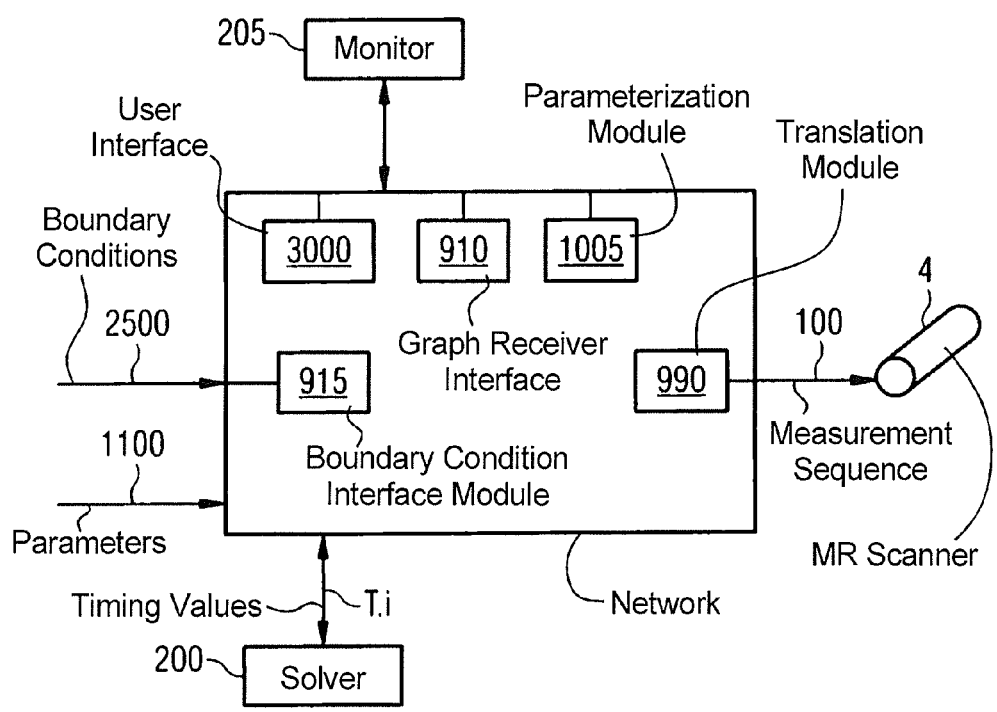
FIG. 8 shows the workflow to create and execute a measurement sequence using the invention.

FIG. 8 shows a block diagram for a system according to a preferred embodiment of the present invention that comprises the two methods according to the invention. The components of the system are connected with one another via solid lines and can communicate among one another. A network in FIG. 8 is represented by the rectangle to which the participating modules are connected. An interaction with the user is possible via a user interface 3000. The user interface 3000 thus comprises the monitor 205 that is suitable to present the directed graph G. The system comprises a graph receiver interface 910 in order to receive the directed graph G. This is provided by the sequence model. Alternatively, the graph receiver interface 910 can receive inputs of the device for formal description. Moreover, the system additionally comprises a boundary condition interface module 915. This receives the boundary conditions 2500 predetermined by the user and/or by the hardware. A parameterization module 1005 determines a parameterization of the measurement sequence 100 using the structure of the directed graph G. The solver 2000 determines from the boundary conditions 2500 and the set of parameters 1100 to be determined a set of timing values T.i that solves the timing problem and comprises permissible values for the set of parameters 1100 to be determined.

Naturally, the solver 2000 could also be used in order to establish all parameters of a measurement sequence 100, for example a resolution of 2 mm within a selected slice. It can prove to be advantageous for the solver 2000 to not predetermine any fixed limits for parameter values, but rather to provide parameter ranges with variable limits in connection with a cost or, respectively, penalty function. How seriously a deviation from predetermined limits will be assessed can be formulated by a penalty function. The solver 2000 then searches for a solution, wherein the variable limits can be altered by the solver 2000 given a simultaneous, optimally minimal penalty function. Only in the event that such a solution is not possible under the predetermined boundary conditions 2500 is an interaction with the user of the MR scanner 4 via the interface 3000 necessary. The user has the possibility to predetermine values for the parameters 1100 to be determined, and/or to predetermine and/or modify the boundary conditions 2500. A complete description of the measurement sequence 100 results from the parameter values determined by the solver 2000. By means of a translation module 990, the measurement sequence 100 can be translated into time slices that can be executed in the MR scanner 4 as part of the system according to the invention.

Overall, the present invention significantly reduces the number of the necessary interactions with the user of the MR scanner 4. Inasmuch the work is simpler not only for the sequence programmer. Moreover, the work of the user of the MR scanner 4 is also significantly simplified. With the present invention he has more time to concentrate on diagnostic questions.

Moreover, a series of entirely new applications results from the selected formal description of the measurement sequence 100. It is thus possible to describe measurement sequences 100 graphically, for example. Moreover, the analysis of measurement sequences 100 is facilitated via the existing, nearly complete parameterization of the measurement sequence 100 by means of the directed graph G. The step of the automatic translation of the existing, complete sequence specification into a programming language as it is conducted by the translation module 990 is easy to realized in a known manner. In the following a specification for a FLASH sequence as it is known to those skilled in the art is provided in XML.

```xml
<?xml version="1.0" encoding="utf-8" ?>
<iSeq xmlns:xsi="http://www.w3.org/2001/XMLSchema-instance"
      xsi:noNamespaceSchemaLocation="iSeq.0.08.xsd" version="0.08"
ID="iSeq_Demo">
   <SubSeq ID="SubSeq_FLASH">
      <XNode ID="XNode_FLASHTxExcite" xcalc="Tx_Excite" tindex="SeqTimeIndex_Tx">
         <PlotInfo>
            <BoundingBox height="40" width="80" x="100" y="260" />
         </PlotInfo>
      </XNode>
      <XNode ID="XNode_FLASHRxGradEcho" xcalc="Rx_GradEcho"

tindex="SeqTimeIndex_Rx">
```

```xml
<PlotInfo>
    <BoundingBox height="40" width="80" x="100" y="460" />
</PlotInfo>
</XNode>
<Entry warp="Warp_ToExcite0" to="XNode_FLASHTxExcite">
    <PlotInfo>
        <EntryBox height="40" width="40" x="60" y="20" />
        <LabelBox height="40" width="80" x="40" y="140" />
        <ToConnectorPoint x="80" y="220" />
        <ToConnectorPoint x="140" y="220" />
    </PlotInfo>
</Entry>
<Connection to="XNode_FLASHRxGradEcho" from="XNode_FLASHTxExcite"
            ctrl="PathCtrl_Always"          warp="Warp_ToGradEcho"
break="false">
    <PlotInfo>
        <LabelBox height="80" width="98" x="100" y="340" />
    </PlotInfo>
</Connection>
<Connection to="XNode_FLASHTxExcite" from="XNode_FLASHRxGradEcho"
            ctrl="PathCtrl_AnotherScan"     warp="Warp_ToExciteN"
break="true">
    <PlotInfo>
        <LabelBox height="120" width="100" x="160" y="60" />
        <FromConnectorPoint x="140" y="540" />
        <FromConnectorPoint x="300" y="540" />
        <FromConnectorPoint x="300" y="20" />
        <FromConnectorPoint x="200" y="20" />
        <ToConnectorPoint x="200" y="220" />
        <ToConnectorPoint x="140" y="220" />
    </PlotInfo>
</Connection>
<Exit ctrl="PathCtrl_Finished" from="XNode_FLASHRxGradEcho">
    <PlotInfo>
        <ExitBox height="40" width="40" x="120" y="660" />
        <LabelBox height="40" width="80" x="100" y="580" />
    </PlotInfo>
</Exit>
```

```xml
<SeqTimeDef time="SeqTime_TE" tindex="SeqTimeIndex_TE">
    <Meas to="XNode_FLASHRxGradEcho" starts="SeqTimeCond_Always"
              ends="SeqTimeCond_Always"
              from="XNode_FLASHTxExcite">
        <PlotInfo>
            <LabelBox height="40" width="40" x="20" y="360" />
            <FromConnectorPoint x="40" y="280" />
            <ToConnectorPoint x="40" y="480" />
            <StartPort right="false" />
            <EndPort right="false" />
        </PlotInfo>
    </Meas>
</SeqTimeDef>
<SeqTimeDef time="SeqTime_TR" tindex="SeqTimeIndex_TR">
    <Meas to="XNode_FLASHTxExcite" starts="SeqTimeCond_NotAtLastScan"
              ends="SeqTimeCond_NotAtFirstScan"
              from="XNode_FLASHTxExcite">
        <PlotInfo>
            <LabelBox height="40" width="40" x="220" y="260" />
            <FromConnectorPoint x="200" y="240" />
            <FromConnectorPoint x="240" y="240" />
            <ToConnectorPoint x="240" y="320" />
            <ToConnectorPoint x="200" y="320" />
            <StartPort right="true" />
            <EndPort right="true" />
        </PlotInfo>
    </Meas>
</SeqTimeDef>
<Reorder IDREF="Reorder_FLASH3d" />
<N4SeqInfo IDREF="N4SeqInfo_BandwidthTimeProductExcite" />
<N4SeqInfo IDREF="N4SeqInfo_DurationExcite" />
<N4SeqInfo IDREF="N4SeqInfo_TimeIndexModeTx" />
<N4SeqInfo IDREF="N4SeqInfo_TimeIndexModeRx" />
<N4SeqInfo IDREF="N4SeqInfo_TimeIndexModeTE" />
<N4SeqInfo IDREF="N4SeqInfo_TimeIndexModeTR" />
<PlotInfo>
    <Font size="12" />
</PlotInfo>
```

```xml
</SubSeq>
<TxBlockCalc ID="Tx_Excite" block="TxBlock_ConstGrad1d">
  <RunFuncParams>
    <BaseMoment IDREF="BaseMoment_Excite" />
    <Property IDREF="Property_SlicePosition" />
    <Property IDREF="Property_BandwidthTimeProductExcite" />
    <Property IDREF="Property_Gamma" />
    <SubSeqGlobalStorage IDREF="SubSeqGlobalStorage_RFSpoil" />
  </RunFuncParams>
</TxBlockCalc>
<RxBlockCalc ID="Rx_GradEcho" block="RxBlock_ConstGrad1d">
  <RunFuncParams>
    <BaseMoment IDREF="BaseMoment_ReadOut" />
    <BaseMoment IDREF="BaseMoment_DeltaPE" />
    <BaseMoment IDREF="BaseMoment_Delta3D" />
    <Property IDREF="Property_DirectionPE" />
    <Property IDREF="Property_Direction3D" />
    <Property IDREF="Property_SlicePosition" />
    <Property IDREF="Property_ImageSamplesRO" />
    <Property IDREF="Property_ImageSamplesPE" />
    <Property IDREF="Property_ImageSamples3D" />
    <Property IDREF="Property_ImagePixelSize2D" />
    <Property IDREF="Property_KSpaceSamplesPE" />
    <Property IDREF="Property_KSpaceSamples3D" />
    <Property IDREF="Property_ImagePixelSize3D" />
    <Property IDREF="Property_OversamplingPE" />
    <Property IDREF="Property_Oversampling3D" />
    <Property IDREF="Property_Gamma" />
    <Property IDREF="Property_NumberOfChannels" />
    <SeqRunIndex IDREF="SeqIndex_Lin" />
    <SeqRunIndex IDREF="SeqIndex_Par" />
    <SubSeqGlobalStorage IDREF="SubSeqGlobalStorage_RFSpoil" />
  </RunFuncParams>
</RxBlockCalc>
<WarpBlockCalc ID="Warp_ToExcite0" block="WarpBlock_WarpM0">
  <RunFuncParams>
    <BaseMoment IDREF="BaseMoment_Zero" />
    <SeqGlobalStorage IDREF="SeqGlobalStorage_M0Store" />
```

```xml
    </RunFuncParams>
  </WarpBlockCalc>
  <WarpBlockCalc ID="Warp_ToExciteN" block="WarpBlock_WarpM0">
    <RunFuncParams>
      <BaseMoment IDREF="BaseMoment_Zero" />
      <SeqGlobalStorage IDREF="SeqGlobalStorage_M0Store" />
    </RunFuncParams>
  </WarpBlockCalc>
  <WarpBlockCalc ID="Warp_ToGradEcho" block="WarpBlock_WarpM0">
    <RunFuncParams>
      <BaseMoment IDREF="BaseMoment_Delta3D" />
      <BaseMoment IDREF="BaseMoment_DeltaPE" />
      <BaseMoment IDREF="BaseMoment_Excite" />
      <BaseMoment IDREF="BaseMoment_ReadOut" />
      <Property IDREF="Property_KSpaceSamples3D" />
      <Property IDREF="Property_KSpaceSamplesPE" />
      <SeqRunIndex IDREF="SeqIndex_Lin" />
      <SeqRunIndex IDREF="SeqIndex_Par" />
      <SeqGlobalStorage IDREF="SeqGlobalStorage_M0Store" />
    </RunFuncParams>
  </WarpBlockCalc>
  <PathCtrlCalc ID="PathCtrl_Finished">
    <RunFuncParams>
      <Property IDREF="Property_KSpaceSamplesPE" />
      <Property IDREF="Property_KSpaceSamples3D" />
      <SeqRunIndex IDREF="SeqIndex_Scan" />
    </RunFuncParams>
  </PathCtrlCalc>
  <PathCtrlCalc ID="PathCtrl_AnotherScan">
    <RunFuncParams>
      <Property IDREF="Property_KSpaceSamplesPE" />
      <Property IDREF="Property_KSpaceSamples3D" />
    </RunFuncParams>
    <SeqRunIndexOut IDREF="SeqIndex_Scan" />
  </PathCtrlCalc>
  <PathCtrlCalc ID="PathCtrl_Always">
    <RunFuncParams />
  </PathCtrlCalc>
```

```xml
<SeqTimeCondCalc ID="SeqTimeCond_NotAtLastScan">
  <RunFuncParams>
    <Property IDREF="Property_KSpaceSamplesPE" />
    <Property IDREF="Property_KSpaceSamples3D" />
    <SeqRunIndex IDREF="SeqIndex_Scan" />
  </RunFuncParams>
</SeqTimeCondCalc>
<SeqTimeCondCalc ID="SeqTimeCond_NotAtFirstScan">
  <RunFuncParams>
    <SeqRunIndex IDREF="SeqIndex_Scan" />
  </RunFuncParams>
</SeqTimeCondCalc>
<SeqTimeCondCalc ID="SeqTimeCond_Always">
  <RunFuncParams />
</SeqTimeCondCalc>
<SeqTimeIndexCalc ID="SeqTimeIndex_Tx">
  <RunFuncParams>
    <Property IDREF="Property_TimeIndexModeTx" />
    <Property IDREF="Property_KSpaceSamplesPE" />
    <Property IDREF="Property_KSpaceSamples3D" />
    <SeqRunIndex IDREF="SeqIndex_Scan" />
  </RunFuncParams>
</SeqTimeIndexCalc>
<SeqTimeIndexCalc ID="SeqTimeIndex_Rx">
  <RunFuncParams>
    <Property IDREF="Property_TimeIndexModeRx" />
    <Property IDREF="Property_KSpaceSamplesPE" />
    <Property IDREF="Property_KSpaceSamples3D" />
    <SeqRunIndex IDREF="SeqIndex_Scan" />
  </RunFuncParams>
</SeqTimeIndexCalc>
<SeqTimeIndexCalc ID="SeqTimeIndex_TE">
  <RunFuncParams>
    <Property IDREF="Property_TimeIndexModeTE" />
    <Property IDREF="Property_KSpaceSamplesPE" />
    <Property IDREF="Property_KSpaceSamples3D" />
    <SeqRunIndex IDREF="SeqIndex_Scan" />
  </RunFuncParams>
```

```xml
</SeqTimeIndexCalc>
<SeqTimeIndexCalc ID="SeqTimeIndex_TR">
  <RunFuncParams>
    <Property IDREF="Property_TimeIndexModeTR" />
    <Property IDREF="Property_KSpaceSamplesPE" />
    <Property IDREF="Property_KSpaceSamples3D" />
    <SeqRunIndex IDREF="SeqIndex_Scan" />
  </RunFuncParams>
</SeqTimeIndexCalc>
<ReorderCalc ID="Reorder_FLASH3d">
  <RunFuncParams>
    <Property IDREF="Property_KSpaceSamplesPE" />
    <SeqRunIndex IDREF="SeqIndex_Scan" />
  </RunFuncParams>
  <SeqRunIndexOut IDREF="SeqIndex_Lin" />
  <SeqRunIndexOut IDREF="SeqIndex_Par" />
</ReorderCalc>
<SeqTime ID="SeqTime_TE" />
<SeqTime ID="SeqTime_TR" />
<TXBlock ID="TxBlock_ConstGrad1d" />
<RXBlock ID="RxBlock_ConstGrad1d" />
<WarpBlock ID="WarpBlock_WarpM0" />
<SeqRunIndex ID="SeqIndex_Scan" />
<SeqRunIndex ID="SeqIndex_Par" />
<SeqRunIndex ID="SeqIndex_Lin" />
<DataType ID="DataType_Int64" />
<DataType ID="DataType_NonNegativeFloat" />
<DataType ID="DataType_UnitVector3dXYZ" />
<DataType ID="DataType_PositiveInteger" />
<DataType ID="DataType_NonNegativeInteger" />
<DataType ID="DataType_PositiveFloat" />
<DataType ID="DataType_SeqTimeVar" />
<DataType ID="DataType_Vector3dXYZ" />
<Unit ID="Unit_SRT" />
<Unit ID="Unit_PercentOver100" />
<Unit ID="Unit_mm" />
<Unit ID="Unit_HzPerPixel" />
<Unit ID="Unit_MHzPerT" />
```

```xml
<Unit ID="Unit_One" />
<Property ID="Property_KSpaceSamples3DCS" DataType="DataType_Int64" Unit="Unit_One" />
<Property ID="Property_SlicePositionCS" DataType="DataType_Int64" Unit="Unit_mm" />
<Property ID="Property_KSpaceSamples3D" DataType="DataType_PositiveInteger" Unit="Unit_One" />
<Property ID="Property_ImagePixelSize3D" DataType="DataType_PositiveFloat" Unit="Unit_mm"
    />
<Property ID="Property_SlicePosition" DataType="DataType_Vector3dXYZ" Unit="Unit_mm" />
<Property ID="Property_ImagePixelSize2D" DataType="DataType_PositiveFloat" Unit="Unit_mm"
    />
<Property                                   ID="Property_Oversampling3D"
    DataType="DataType_NonNegativeFloat"
        Unit="Unit_PercentOver100" />
<Property                                   ID="Property_KSpaceSamplesPE"
    DataType="DataType_PositiveInteger"
        Unit="Unit_One" />
<Property                                   ID="Property_BandwidthTimeProductExcite"
    DataType="DataType_PositiveFloat"
        Unit="Unit_One" />
<Property ID="Property_Gamma" DataType="DataType_PositiveFloat" Unit="Unit_MHzPerT" />
<Property                                   ID="Property_OversamplingPE"
    DataType="DataType_NonNegativeFloat"
        Unit="Unit_PercentOver100" />
<Property                                   ID="Property_ImageSamples3D"
    DataType="DataType_PositiveInteger"
        Unit="Unit_One" />
<Property ID="Property_Direction3D" DataType="DataType_UnitVector3dXYZ" Unit="Unit_One"
    />
<Property                                   ID="Property_NumberOfChannels"
    DataType="DataType_PositiveInteger"
        Unit="Unit_One" />
```

```xml
<Property                                    ID="Property_ImageSamplesRO"
DataType="DataType_PositiveInteger"
    Unit="Unit_One" />
<Property                                    ID="Property_ImageSamplesPE"
DataType="DataType_PositiveInteger"
    Unit="Unit_One" />
<Property ID="Property_DirectionRO" DataType="DataType_UnitVector3dXYZ"
Unit="Unit_One"
    />
<Property ID="Property_DirectionPE" DataType="DataType_UnitVector3dXYZ"
Unit="Unit_One"
    />
<Property                                    ID="Property_TimeIndexModeTx"
DataType="DataType_NonNegativeInteger"
    Unit="Unit_One" />
<Property                                    ID="Property_TimeIndexModeRx"
DataType="DataType_NonNegativeInteger"
    Unit="Unit_One" />
<Property                                    ID="Property_TimeIndexModeTE"
DataType="DataType_NonNegativeInteger"
    Unit="Unit_One" />
<Property                                    ID="Property_TimeIndexModeTR"
DataType="DataType_NonNegativeInteger"
    Unit="Unit_One" />
<N4SeqInfo       ID="N4SeqInfo_BandwidthTimeProductExcite"       DataType="DataType_PositiveFloat"
    Unit="Unit_One" />
<N4SeqInfo                                   ID="N4SeqInfo_DurationExcite"
DataType="DataType_NonNegativeInteger"
    Unit="Unit_SRT" />
<N4SeqInfo                                   ID="N4SeqInfo_TimeIndexModeTx"
DataType="DataType_NonNegativeInteger"
    Unit="Unit_One" />
<N4SeqInfo                                   ID="N4SeqInfo_TimeIndexModeRx"
DataType="DataType_NonNegativeInteger"
    Unit="Unit_One" />
<N4SeqInfo                                   ID="N4SeqInfo_TimeIndexModeTE"
DataType="DataType_NonNegativeInteger"
```

```xml
      Unit="Unit_One" />
<N4SeqInfo                                    ID="N4SeqInfo_TimeIndexModeTR"
DataType="DataType_NonNegativeInteger"
      Unit="Unit_One" />
<BaseMomentCalc ID="BaseMoment_Zero" />
<BaseMomentCalc ID="BaseMoment_Excite">
   <Property IDREF="Property_Direction3D" />
   <Property IDREF="Property_BandwidthTimeProductExcite" />
   <Property IDREF="Property_ImagePixelSize3D" />
   <Property IDREF="Property_ImageSamples3D" />
   <Property IDREF="Property_Gamma" />
</BaseMomentCalc>
<BaseMomentCalc ID="BaseMoment_ReadOut">
   <Property IDREF="Property_DirectionRO" />
   <Property IDREF="Property_ImagePixelSize2D" />
   <Property IDREF="Property_ImageSamplesRO" />
   <Property IDREF="Property_Gamma" />
</BaseMomentCalc>
<BaseMomentCalc ID="BaseMoment_DeltaPE">
   <Property IDREF="Property_DirectionPE" />
   <Property IDREF="Property_Gamma" />
   <Property IDREF="Property_OversamplingPE" />
   <Property IDREF="Property_ImageSamplesPE" />
   <Property IDREF="Property_ImagePixelSize2D" />
</BaseMomentCalc>
<BaseMomentCalc ID="BaseMoment_Delta3D">
   <Property IDREF="Property_Direction3D" />
   <Property IDREF="Property_Gamma" />
   <Property IDREF="Property_Oversampling3D" />
   <Property IDREF="Property_ImageSamples3D" />
   <Property IDREF="Property_ImagePixelSize3D" />
</BaseMomentCalc>
<SeqGlobalStorage ID="SeqGlobalStorage_M0Store" />
<SubSeqGlobalStorage ID="SubSeqGlobalStorage_RFSpoil" />
</iSeq>
```

The XML provided above describes the FLASH sequence with regard to the directed graph G given in Figure 6. The moments for each of the X blocks X can also be determined from the formal description including the entire sequence equations (as well as the equations for the gradient moments). For example, in the following the source code is specified in C++ for the individual variables which describe a FLASH sequence.

Gradient moment in 3D direction, BaseMoment_Delta3D

```
#ifdef GET_MANUAL_INCLUDE
#include "GradCalc.h"
endif ifdef GET_MANUAL_BODY
double myDeltaM0;

Success = GradCalc::deltaMoment (myDeltaM0,
            PROPERTY(Gamma),

PROPERTY(ImageSamples3D)*PROPERTY(ImagePixelSize3D),
            PROPERTY(Oversampling3D)
                );
CHECK_SUCCESS (Success, false);

BASEMOMENT(Delta3D).setDirection(PROPERTY(Direction3D));
BASEMOMENT(Delta3D).setValue(myDeltaM0);

Success=true;
#endif
```

Gradient moment in phase coding direction, Base_MomentDeltaPE [sic?]

```
#ifdef GET_MANUAL_INCLUDE
#include "GradCalc.h"
endif ifdef GET_MANUAL_BODY
double myDeltaM0;
```

```
Success = GradCalc::deltaMoment (myDeltaM0,
            PROPERTY(Gamma),

PROPERTY(ImageSamplesPE)*PROPERTY(ImagePixelSize2D),
            PROPERTY(OversamplingPE)
                );
CHECK_SUCCESS (Success, false);

BASEMOMENT(DeltaPE).setDirection(PROPERTY(DirectionPE));
BASEMOMENT(DeltaPE).setValue(myDeltaM0);

Success=true;
#endif
```

Gradient moment excitation, BaseMoment_Excite

```
#ifdef GET_MANUAL_INCLUDE
#include "GradCalc.h"
endif ifdef GET_MANUAL_BODY
double myGSAmpl;
int64_t myCalcDuration = 25600;

Success       =      GradCalc::constGSAmplitude     (
static_cast<uint64_t>(myCalcDuration),
            PROPERTY(BandwidthTimeProductExcite),
            PROPERTY(ImageSamples3D)             *
PROPERTY(ImagePixelSize3D),
            PROPERTY(Gamma),
            myGSAmpl
                );
CHECK_SUCCESS (Success, false);

BASEMOMENT(Excite).setDirection(PROPERTY(Direction3D));
BASEMOMENT(Excite).setValue(myGSAmpl*static_cast<double>(myCal
cDuration));
```

```
Success=true;
#endif
```

Gradient moment in readout direction, BaseMoment_ReadOut

```
#ifdef GET_MANUAL_INCLUDE
#include "GradCalc.h"
endif ifdef GET_MANUAL_BODY
double myDeltaM0;

Success = GradCalc::deltaMoment (  myDeltaM0,
                PROPERTY(Gamma),

PROPERTY(ImagePixelSize2D)*PROPERTY(ImageSamplesRO),
                0.0
                );
CHECK_SUCCESS (Success, false);

BASEMOMENT(ReadOut).setDirection (PROPERTY(DirectionRO));
BASEMOMENT(ReadOut).setValue
(myDeltaM0*static_cast<double>(PROPERTY(ImageSamplesRO)));

Success=true;
#endif
```

Zeroth Moment, BaseMoment_Zero

```
#ifdef GET_MANUAL_INCLUDE
endif ifdef GET_MANUAL_BODY
BASEMOMENT(Zero).setDirection(vec3(0,0,1));
BASEMOMENT(Zero).setValue(0);
```

```
Success=true;
#endif
```

FLASH sub-sequence source code for configuration of an X block X,

Excitation pulse, Tx_Excite

```
#ifdef GET_MANUAL_INCLUDE
endif ifdef GET_MANUAL_BODY
CTRL_STRUCT(AdditionalPhase)                              =
90+SUBSEQGLOBALSTORAGE(RFSpoil).CurrentPhase;
CTRL_STRUCT(Asymmetry) = 0.5;
CTRL_STRUCT(BandwidthTimeProduct)                         =
PROPERTY(BandwidthTimeProductExcite);
CTRL_STRUCT(FlipAngle) = 90;
CTRL_STRUCT(Gamma) = PROPERTY(Gamma);
CTRL_STRUCT(SlicePosition) = PROPERTY(SlicePosition);

Success          =           CTRL_STRUCT(M0).addBaseMoment
(BASEMOMENT(Excite), 1.0);
CHECK_SUCCESS (Success, false);
#endif
```

Gradient echo readout, Rx_GradEcho

```
#ifdef GET_MANUAL_INCLUDE
#include "GradCalc.h"
#include "FreqPhaseCalc.h"
#include "StdRxCtrlSettings.h"
endif ifdef GET_MANUAL_BODY
double myPhaseIncPE;
```

```
Success = FreqPhaseCalc::KSpacePhaseInc
    (
        myPhaseIncPE,
        PROPERTY(DirectionPE)*PROPERTY(SlicePosition), PROPERTY(ImagePixelSize2D)*PROPERTY(ImageSamplesPE),
        PROPERTY(OversamplingPE)
    );
CHECK_SUCCESS (Success, false);

double myPhaseInc3D;

Success = FreqPhaseCalc::KSpacePhaseInc
    (
        myPhaseInc3D,
        PROPERTY(Direction3D)*PROPERTY(SlicePosition), PROPERTY(ImagePixelSize3D)*PROPERTY(ImageSamples3D),
        PROPERTY(Oversampling3D)
    );
CHECK_SUCCESS (Success, false);

double myAdditionalPhase = 0;

int32_t myCenterLinNo = PROPERTY(KSpaceSamplesPE)/2;
int32_t myCenterParNo = PROPERTY(KSpaceSamples3D)/2;

int32_t    myLinNo    =    static_cast<int32_t>(SUBSEQINDEX(Lin))  -
myCenterLinNo;
int32_t    myParNo    =    static_cast<int32_t>(SUBSEQINDEX(Par))  -
myCenterParNo;

Success = FreqPhaseCalc::applyPEOffcenter
    (
        myAdditionalPhase,
        FreqPhaseCalc::ADCAppliesPhase,
        myPhaseIncPE,
        myLinNo,
```

```
            myPhaseInc3D,
            myParNo
        );
CHECK_SUCCESS (Success, false);

double myDeltaM0PE;

Success = GradCalc::deltaMoment
        (
            myDeltaM0PE,
            PROPERTY(Gamma), PROPERTY(ImagePixelSize2D)*PROPERTY(ImageSamplesPE),
            PROPERTY(OversamplingPE)
        );
CHECK_SUCCESS (Success, false);

double myDeltaM03D;

Success = GradCalc::deltaMoment
        (
            myDeltaM03D,
            PROPERTY(Gamma), PROPERTY(ImagePixelSize3D)*PROPERTY(ImageSamples3D),
            PROPERTY(Oversampling3D)
        );
CHECK_SUCCESS (Success, false);

myAdditionalPhase                                              +=
SUBSEQGLOBALSTORAGE(RFSpoil).CurrentPhase;

SUBSEQGLOBALSTORAGE(RFSpoil).NextPhaseInc += 50;
SUBSEQGLOBALSTORAGE(RFSpoil).CurrentPhase                      +=
SUBSEQGLOBALSTORAGE(RFSpoil).NextPhaseInc;

CTRL_STRUCT(AdditionalPhase) = myAdditionalPhase;
CTRL_STRUCT(Gamma) = PROPERTY(Gamma);
```

```
CTRL_STRUCT(SlicePosition) = PROPERTY(SlicePosition);
CTRL_STRUCT(ReadOutImageSamples)              =
PROPERTY(ImageSamplesRO);
CTRL_STRUCT(PartialFourierFactor) = 1.0;

CTRL_STRUCT(EchoSpec).push_back(ExcitationRF);

Success        =         CTRL_STRUCT(M0).addBaseMoment
(BASEMOMENT(ReadOut), 1.0);
CHECK_SUCCESS (Success, false);

Success        =      CTRL_STRUCT(EchoM0).addBaseMoment
(BASEMOMENT(DeltaPE), myLinNo);
CHECK_SUCCESS (Success, false);

Success        =      CTRL_STRUCT(EchoM0).addBaseMoment
(BASEMOMENT(Delta3D), myParNo);
CHECK_SUCCESS (Success, false);
#endif
```

FLASH sub-sequence source code for configuration of a warp block W

Warp block "ToExcite0" for first excitation, Warp_ToExcite0

```
#ifdef GET_MANUAL_INCLUDE
endif ifdef GET_MANUAL_BODY
if (SEQGLOBALSTORAGE(M0Store).LKBaseMoment().isEmpty())
{
    Success = rCtrl.M0.addBaseMoment (BASEMOMENT(Zero), 1);
    CHECK_SUCCESS (Success,false);
}
else
{
    Success       =      rCtrl.M0.addBaseMomentLinearCombination
(SEQGLOBALSTORAGE(M0Store).LKBaseMoment());
```

```
        CHECK_SUCCESS (Success,false);

SEQGLOBALSTORAGE(M0Store).LKBaseMoment().clear();
    }
    #endif
```

Warp block "ToExciteN" for first excitation, Warp_ToExciteN

```
    #ifdef GET_MANUAL_INCLUDE
    #endif ifdef GET_MANUAL_BODY
    if (SEQGLOBALSTORAGE(M0Store).LKBaseMoment().isEmpty())
    {
        Success = rCtrl.M0.addBaseMoment (BASEMOMENT(Zero), 1);
        CHECK_SUCCESS (Success,false);
    }
    else
    {
        Success       =       rCtrl.M0.addBaseMomentLinearCombination
    (SEQGLOBALSTORAGE(M0Store).LKBaseMoment());
        CHECK_SUCCESS (Success,false);

SEQGLOBALSTORAGE(M0Store).LKBaseMoment().clear();
    }
    #endif
```

Warp block "ToGradEcho" for first excitation, Warp_ ToGradEcho

```
    #ifdef GET_MANUAL_INCLUDE
    #endif ifdef GET_MANUAL_BODY
    int64_t myLinNo = SUBSEQINDEX(Lin);
    int64_t myParNo = SUBSEQINDEX(Par);
    int64_t myCenterLinNo = PROPERTY(KSpaceSamplesPE)/2;
    int64_t myCenterParNo = PROPERTY(KSpaceSamples3D)/2;
```

```
Success            =    CTRL_STRUCT(M0).addBaseMoment
(BASEMOMENT(DeltaPE), myLinNo - myCenterLinNo);
CHECK_SUCCESS (Success,false);

Success            =    CTRL_STRUCT(M0).addBaseMoment
(BASEMOMENT(Delta3D), myParNo - myCenterParNo);
CHECK_SUCCESS (Success,false);

Success            =    CTRL_STRUCT(M0).addBaseMoment
(BASEMOMENT(Excite), -0.5);
CHECK_SUCCESS (Success,false);

Success            =    CTRL_STRUCT(M0).addBaseMoment
(BASEMOMENT(ReadOut), -0.5);
CHECK_SUCCESS (Success,false);

Success                                                =
SEQGLOBALSTORAGE(M0Store).LKBaseMoment().addBaseMoment
(BASEMOMENT(DeltaPE),   static_cast<double>(myCenterLinNo)  -
static_cast<double>(SUBSEQINDEX(Lin)));
CHECK_SUCCESS (Success,false);

Success                                                =
SEQGLOBALSTORAGE(M0Store).LKBaseMoment().addBaseMoment
(BASEMOMENT(Delta3D),   static_cast<double>(myCenterParNo)  -
static_cast<double>(SUBSEQINDEX(Par)));
CHECK_SUCCESS (Success,false);

Success                                                =
SEQGLOBALSTORAGE(M0Store).LKBaseMoment().addBaseMoment
(BASEMOMENT(ReadOut), 0.5);
CHECK_SUCCESS (Success,false);
#endif
```

FLASH sub-sequence source code: path controls

Path controls that are always to be satisfied, "Always"

```
#ifdef GET_MANUAL_INCLUDE
endif ifdef GET_MANUAL_BODY
TAKE_THIS_PATH(true);
Success=true;
#endif
```

Path controls "Additional scan?", "AnotherScan"

```
#ifdef GET_MANUAL_INCLUDE
endif ifdef GET_MANUAL_BODY
if         (SUBSEQINDEX(Scan)        <
PROPERTY(KSpaceSamplesPE)*PROPERTY(KSpaceSamples3D)-1)
{
   TAKE_THIS_PATH(true);
   SUBSEQINDEX(Scan)++;
}
else
{
   TAKE_THIS_PATH(false);
}

Success=true;
#endif
```

Path control to end, "Finished"

```
#ifdef GET_MANUAL_INCLUDE
#ifdef iSeqDemo_KsmStorageSingleton
#include "KsmStorageSingleton.h"
#include "KsmStorageSingletonString.h"
#endif
#endif
```

```
#ifdef GET_MANUAL_BODY
if      (SUBSEQINDEX(Scan)      ==
PROPERTY(KSpaceSamplesPE)*PROPERTY(KSpaceSamples3D)-1)
{
   TAKE_THIS_PATH(true);
}
else
{
   TAKE_THIS_PATH(false);
}

Success=true;

#ifdef iSeqDemo_KsmStorageSingleton
{
   KsmStorageSingletonString      myKey      =
KsmStorageSingletonString("demo message from Reorder_FLASH3d");

IKsmStorageSingletonEntry    *    myEntryPtr    =
KsmStorageSingleton::getObject(myKey);

if (myEntryPtr)
   {
      KsmStorageSingletonString    *    pStr    =
dynamic_cast<KsmStorageSingletonString*>(myEntryPtr);

if (pStr)
      {
         PR_INFO ("\'%s\'= \'%s\'", myKey.str.c_str(), pStr->str.c_str());
      }
      else
      {
         PR_WARN ("\'%s\' from KsmStorageSingleton is of wrong type",
            myKey.str.c_str());
      }
   }
   else
```

```
        {
            PR_WARN ("can not get \'%s\' from KsmStorageSingleton",
myKey.str.c_str());
        }
    }
#endif
#endif
```

FLASH sub-sequence source code: conditions for sequence time measurement

Time measurement condition "always", SeqTimeCond_Always

```
        #ifdef GET_MANUAL_INCLUDE
        #endif ifdef GET_MANUAL_BODY
        SET_SEQ_TIME_MARK(true);
        Success = true;
        #endif
```

Time measurement condition "not at first scan", SeqTimeCond_NotAtFirstScan

```
        #ifdef GET_MANUAL_INCLUDE
        #endif ifdef GET_MANUAL_BODY
        SET_SEQ_TIME_MARK(SUBSEQINDEX(Scan)!=0);
        Success = true;
        #endif
```

Time measurement condition "not at last scan", SeqTimeCond_NotAtLastScan

```
        #ifdef GET_MANUAL_INCLUDE
        #endif ifdef GET_MANUAL_BODY
```

```
    SET_SEQ_TIME_MARK(SUBSEQINDEX(Scan)+1                              !=
    PROPERTY(KSpaceSamplesPE)*PROPERTY(KSpaceSamples3D));
    Success = true;
#endif
```

Initialization of the index, SeqTimeIndex_AlwaysZero

```
#ifdef GET_MANUAL_INCLUDE
endif ifdef GET_MANUAL_BODY
    SET_SEQ_TIME_INDEX(0);
    Success = true;
#endif
```

The method according to the invention can provide, due to the automatic translation of the formal description of a sequence description for a measurement sequence 100, information (instructions) that can be directly used in current hardware of an MR scanner 4. Therefore the methods according to the invention can be seamlessly employed in current MR scanners 4.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for formalized description of a measurement sequence, said measurement sequence being executable by a magnetic resonance scanner, said method comprising the steps of:
    formulating a sequence model for a measurement sequence, said sequence model being comprised of blocks selected from the group consisting of a warp block and an X block, and a pause block, and depicting said sequence model as a directed graph comprising at least nodes, edges between said nodes, and properties of said edges for workflow control of the directed graph, said nodes being formed from the group consisting of said X blocks, an entrance point, and an exit point;
    providing said sequence model to a processor and, in said processor, automatically parameterizing said measurement sequence using said directed graph, except for a predetermined set of parameters that must still be parameterized; and
    making the measurement sequence, parameterized from said directed graph except for said predetermined set of parameters, available from said processor as an output.

2. A method as claimed in claim 1 comprising designating said properties of said edges for workflow control from the group consisting of said warp block, a time measurement, said pause block, and a path control.

3. A method as claimed in claim 2 comprising, in said processor, permitting only one path control in said directed graph to be fulfilled at a time.

4. A method as claimed in claim 2 comprising selecting each time measurement from the group consisting of a time duration of an X block, a sequence time measured between centers of two of said X blocks, and a sequence start time representing a point in time of a center of a first X block within a measurement sequence.

5. A method as claimed in claim 1 comprising selecting said edges from the group consisting of a transition from the entrance point via a path control to a warp block and then to an X block, a transition from an X block via a path control to the exit point, a transition from an X block via a path control to a warp block and then to an X block, a transition from an X block via a path control and a pause to a warp block and then to an X block, and a transition from an X block via a time measurement to an X block.

6. A method as claimed in claim 1 comprising defining every X block as a time slice selected from the group consisting of a reception type time slice and a transmission type time slice.

7. A method as claimed in claim 6 comprising defining said X block as a transmission type X block representing at least one of an inversion pulse, an excitation pulse, a refocusing pulse, and a hybrid form pulse.

8. A method as claimed in claim 1 comprising, in said processor:
    automatically determining indices for each X block in said directed graph;
    automatically determining variable for each warp block and each X block from the directed graph; and
    automatically determining gradient movements of the zeroth order for each center of each X block from said directed graph, each X block being selected from the group consisting of transmission type X blocks and reception type X blocks.

9. A method as claimed in claim 1 comprising automatically determining sequence equations in said processor from said directed graph.

10. A method as claimed in claim 1 comprising, in said processor, automatically determining, from said directed graph, a path for creation of an echo signal for each X block, each X block being selected from the group consisting of transmission type X blocks and reception type X block, as a series of pulse selected from the group consisting of a series of excitation pulses, a series of refocusing pulses, a series of hybrid form pulses, and a series of inversion pulses.

11. A method as claimed in claim 1 comprising, in said processor, automatically determining gradient movements from said directed graph, said gradient moments being of the first order for each center of each X block, each X block being selected from the group consisting of transmission type X blocks and reception type X blocks, said gradient moments allowing flux compensation or flux coding to be introduced into said measurement sequence.

12. A method as claimed in claim 1 comprising, in said processor, automatically determining, from said directed graph, diffusions weightings for each X block, each X block being selected from the group consisting of transmission type X blocks and reception type X blocks.

13. A method as claimed in claim 1 comprising, in said processor, determining, from said directed graph, gradient moments of an order higher than the first order for each center of each X block, each X block being selected from the group consisting of transmission type X blocks and reception type X blocks.

14. A method as claimed in claim 1 comprising, in said processor, determining sub-sequences within said measurement sequence; and
    designating indivisible super blocks within each determined sub-sequence, and representing said indivisible super blocks in a directed graph connected via a sequence time.

15. A method for formalized description of a measurement sequence, said measurement sequence being executable by a magnetic resonance scanner, said method comprising the steps of:
    formulating a sequence model for a measurement sequence, said sequence model being comprised of blocks selected from the group consisting of a warp block and an X block, and a pause block, and depicting said sequence model as a directed graph comprising at least nodes, edges between said nodes, and properties of said edges for workflow control of the directed graph, said nodes being formed from the group consisting of said X blocks, an entrance point, and an exit point;
    providing said sequence model to a processor and, in said processor, automatically parameterizing said measurement sequence using said directed graph, except for a predetermined set of parameters that must still be parameterized;
    making the measurement sequence, parameterized from said directed graph except for said predetermined set of parameters, available from said processor as an output;

providing said measurement sequence parameterized from said directed graph, except for said predetermined set of parameters, to a solver;

providing boundary conditions to said solver that must be satisfied for execution of said measurement sequence by said magnetic resonance scanner;

in said solver, automatically determining, dependent on said boundary conditions, timing values for each warp block and each X block in said measurement sequence, and determining permissible values for said predetermined set of parameters, to generate a complete formal description of said measurement sequence comprising said measurement sequence parameterized from said directed graph, said timing values, and said permissible values for said predetermined set of parameters; and in said solver, automatically translating said formal description of said measurement sequence into a series of time slices in a form executable by said magnetic resonance scanner, and making said series of time slices available at an output of said solver.

16. A method as claimed in claim 15 comprising, for interleaved execution of multiple measurement sequences by said magnetic resonance scanner, identifying, in said solver, a sub-sequence in a first of said multiple measurement sequences that comprises pauses, and identifying sub-sequences in others of said multiple measurement sequences that are executable, without overlap, during said pauses of said first of said multiple measurement sequences.

17. A method as claimed in claim 15 comprising selecting said boundary conditions from the group consisting of contrast specifications for an image generated by said magnetic resonance scanner, image resolution specifications for an image generated by said magnetic resonance scanner, position specifications for at least one slice to be imaged by said magnetic resonance scanner, hardware limitations of said magnetic resonance scanner, minimization of measurement time for executing said measurement sequence, and patient specifications for a patient to be examined in said magnetic resonance scanner using said measurement sequence.

18. A method as claimed in claim 15 comprising, in said solver, automatically translating said formal description of said measurement sequence into a programming language in a form executable by a control unit associated with said magnetic resonance scanner.

19. A device for formalized description of a measurement sequence, said measurement sequence being executable by a magnetic resonance scanner, said device comprising:

a sequence model interface configured to receive a sequence model for a measurement sequence, said sequence model being comprised of blocks selected from the group consisting of a warp block and an X block, and a pause block;

a processor that generates and depicts said sequence model as a directed graph comprising at least nodes, edges, between said nodes, and properties of said edges for workflow control of the directed graph, said nodes being formed from the group consisting of said X blocks, an entrance point, and an exit point;

said processor comprising a parameterization module that automatically parameterizes said measurement sequence using said directed graph, except for a predetermined set of parameters that must still be parameterized; and said processor being configured to make the measurement sequence, parameterized from said directed graph except for said predetermined set of parameters, available from said processor as an output.

20. A device for formalized description of a measurement sequence, said measurement sequence being executable by a magnetic resonance scanner, said device comprising the steps of:

a sequence model interface configured to receive a sequence model for a measurement sequence, said sequence model being comprised of blocks selected from the group consisting of a warp block and an X block and a pause block;

a processor that generates and depicts at a monitor associated with said processor, said sequence model as a directed graph comprising at least nodes, edges, between said nodes, and properties of said edges for workflow control of the directed graph, said nodes being formed from the group consisting of said X blocks, an entrance point, and an exit point;

comprising a parameterization module that said processor automatically parameterizes said measurement sequence using said directed graph, except for a predetermined set of parameters that must still be parameterized;

said processor being configured to make the measurement sequence, parameterized from said directed graph except for said predetermined set of parameters, available from said processor as an output;

a solver having a measurement sequence interface configured to receive said measurement sequence parameterized from said directed graph, accept for said predetermined set of parameters, from said processor;

said solver comprising a boundary conditions interface configured to receive boundary conditions that must be satisfied for execution of said measurement sequence by said magnetic resonance scanner;

said solver being configured to automatically determine, dependent on said boundary conditions, timing values for each warp block and each X block in said measurement sequence, and to determine permissible values for said predetermined set of parameters, to generate a complete formal description of said measurement sequence comprising said measurement sequence parameterized from said directed graph, said timing values, and said permissible values for said predetermined set of parameters; and said solver being configured to automatically translate said formal description of said measurement sequence into a series of time slices in a form executable by said magnetic resonance scanner, and to make said series of time slices available at an output of said solver.

21. A device as claimed in claim 20 comprising at least one additional module selected from the group consisting of:

an indexing module configured to determine indices for each block in said directed graph;

a variable module configured to determine variables for each warp block or each X block from said directed graph;

a sequence equation module configured to determine sequence equations from said directed graph;

an echo path module configured to determine, from said directed graph, a path for creation of an echo signal for each X block, each X block being selected from the group consisting of transmission type X blocks and reception type X blocks, as a series of pulses selected from the group consisting of a series of excitation pulses, a series of refocusing pulses, a series of hybrid form pulses, and a series of inversion pulses;

a gradient moment module configured to determine, from said directed graph, a gradient moment having an order selected from the consisting of the zeroth order, the first order, and an order higher than the first order, for each X block, each X block being selected from the group consisting of transmission type X blocks and reception type X blocks;

a diffusion weighting module configured to determine, from said directed graph, diffusion weightings for each X block, each X block being selected from the group consisting of transmission type X blocks and reception type X blocks;

a limitation module configured to receive multiple measurement sequences to be executed in a limited manner by said magnetic resonance scanner;

a sub-sequence definition module configured to identify at least one sub-sequence comprising pauses within a first measurement sequence in multiple measurement sequences and that determines sub-sequences in other measurement sequences in said multiple measurement sequences allowing interleaved execution of said sub-sequences.

22. A non-transitory computer-readable medium encoded with programming instructions for formalized description of a measurement sequence, said measurement sequence being executable by a magnetic resonance scanner, said programming instructions causing computerized devices to:

formulate a sequence model for a measurement sequence, said sequence model being comprised of blocks selected from the group consisting of a warp block and an X block, and a pause block, and depict said sequence model as a directed graph comprising at least nodes, edges between said nodes, and properties of said edges for workflow control of the directed graph, said nodes being formed from the group consisting of said X blocks, an entrance point, and an exit point;

automatically parameterize said measurement sequence using said directed graph, except for a predetermined set of parameters that must still be parameterized; and make the measurement sequence, parameterized from said directed graph except for said predetermined set of parameters, available as an output from one of said computerized devices.

23. A non-transitory computer-readable medium encoded with program instructions for formalized description of a measurement sequence, said measurement sequence being executable by a magnetic resonance scanner, said method said programming instructions causing computerized devices to:

formulate a sequence model for a measurement sequence, said sequence model being comprised of blocks selected from the group consisting of a warp block and an X block, and a pause block, and depict said sequence model as a directed graph comprising at least nodes, edges between said nodes, and properties of said edges for workflow control of the directed graph, said nodes being formed from the group consisting of said X blocks, an entrance point, and an exit point;

automatically parameterize said measurement sequence using said directed graph, except for a predetermined set of parameters that must still be parameterized;

automatically determine, dependent on said boundary conditions, timing values for each warp block and each X block in said measurement sequence, and determining permissible values for said predetermined set of parameters, to generate a complete formal description of said measurement sequence comprising said measurement sequence parameterized from said directed graph, said timing values, and said permissible values for said predetermined set of parameters; and automatically translate said formal description of said measurement sequence into a series of time slices in a form executable by said magnetic resonance scanner, and make said series of time slices available at an output from one of said computerized devices.

24. A magnetic resonance system comprising:

a magnetic resonance scanner having a control unit;

a sequence model interface configured to receive a sequence model for a measurement sequence executable by said magnetic resonance scanner, said sequence model being comprised of blocks selected from the group consisting of a warp block and an X block and a pause block;

a processor that generates and depicts at a monitor associated with said processor, said sequence model as a directed graph comprising at least nodes, edges, between said nodes, and properties of said edges for workflow control of the directed graph, said nodes being formed from the group consisting of said X blocks, an entrance point, and an exit point;

comprising a parameterization module that said processor automatically parameterizes said measurement sequence using said directed graph, except for a predetermined set of parameters that must still be parameterized;

said processor being configured to make the measurement sequence, parameterized from said directed graph except for said predetermined set of parameters, available from said processor as an output;

a solver having a measurement sequence interface configured to receive said measurement sequence parameterized from said directed graph, accept for said predetermined set of parameters, from said processor;

said solver comprising a boundary conditions interface configured to receive boundary conditions that must be satisfied for execution of said measurement sequence by said magnetic resonance scanner;

said solver being configured to automatically determine, dependent on said boundary conditions, timing values for each warp block and each X block in said measurement sequence, and to determine permissible values for said predetermined set of parameters, to generate a complete formal description of said measurement sequence comprising said measurement sequence parameterized from said directed graph, said timing values, and said permissible values for said predetermined set of parameters;

said solver being configured to automatically translate said formal description of said measurement sequence into a series of time slices in a form executable by said magnetic resonance scanner, and to supply said series of time slices in said form to said control unit; and said control unit operating said magnetic resonance scanner according to the time slices supplied thereto by said solver.

* * * * *